US010463410B2

United States Patent
Goodwin, Jr. et al.

(10) Patent No.: US 10,463,410 B2
(45) Date of Patent: Nov. 5, 2019

(54) BONE PLATE HAVING A CONNECTOR AND A CONNECTOR FOR A SURGICAL LOOP

(71) Applicant: A&E Advanced Closure Systems, LLC, Los Angeles, CA (US)

(72) Inventors: Robert A. Goodwin, Jr., Marquette, MI (US); Matthew P. Gephart, Marquette, MI (US)

(73) Assignee: A&E Advanced Closure Systems, LLC, Los Angeles, CA (US)

( * ) Notice: Subject to any disclaimer, the term of this patent is extended or adjusted under 35 U.S.C. 154(b) by 101 days.

(21) Appl. No.: 15/411,682

(22) Filed: Jan. 20, 2017

(65) Prior Publication Data
US 2017/0209190 A1    Jul. 27, 2017

Related U.S. Application Data

(60) Provisional application No. 62/286,145, filed on Jan. 22, 2016.

(51) Int. Cl.
*A61B 17/82* (2006.01)
*A61B 17/80* (2006.01)

(52) U.S. Cl.
CPC .......... *A61B 17/8004* (2013.01); *A61B 17/82* (2013.01)

(58) Field of Classification Search
CPC ... A61B 17/8004; A61B 17/82; A61B 17/823; A61B 17/826; A61B 17/842; A61B 17/8076
See application file for complete search history.

(56) References Cited

U.S. PATENT DOCUMENTS

| | | |
|---|---|---|
| 1,988,534 A | 1/1935 | Joseph |
| 2,002,977 A | 5/1935 | Carr |
| 2,557,877 A | 6/1951 | Kluson |

(Continued)

FOREIGN PATENT DOCUMENTS

| | | |
|---|---|---|
| AU | 743254 | 1/2002 |
| CN | 201260694 Y | 6/2009 |

(Continued)

OTHER PUBLICATIONS

International Search Report and Written Opinion of related International Patent Application No. PCT/US17/14386, dated Apr. 14, 2017, 24 pages.

(Continued)

*Primary Examiner* — Matthew J Lawson
(74) *Attorney, Agent, or Firm* — Fitch, Even, Tabin & Flannery LLP

(57) ABSTRACT

In accordance with one aspect of the present disclosure, an apparatus for securing bone portions is provided that includes a surgical cable having a plurality of elongate elements and a connector. The connector includes a body and a deformable sleeve associated with the body and having a through opening for receiving the surgical cable. The through opening of the surgical cable has a non-deformed configuration sized to compress the elements of the surgical cable together with the surgical cable extending in the sleeve through opening. An actuator is connected to the body and is operable to deform the sleeve and further compress the compressed elements of the surgical cable therein to secure the surgical cable relative to the body.

24 Claims, 25 Drawing Sheets

(56) References Cited

U.S. PATENT DOCUMENTS

| | | |
|---|---|---|
| 3,959,960 A | 6/1976 | Santos |
| 4,050,464 A | 9/1977 | Hall |
| 4,184,784 A | 1/1980 | Killian |
| 4,269,180 A | 5/1981 | Dall |
| 4,327,715 A | 5/1982 | Corvisier |
| 4,583,541 A | 4/1986 | Barry |
| 4,959,065 A | 9/1990 | Arnett |
| 4,966,600 A | 10/1990 | Songer |
| 5,015,248 A | 5/1991 | Burstein |
| 5,139,498 A | 8/1992 | AstudilloLey |
| 5,312,410 A | 5/1994 | Miller |
| 5,395,374 A | 3/1995 | Miller |
| 5,415,658 A | 5/1995 | Kilpela |
| 5,449,361 A | 9/1995 | Preissman |
| 5,456,722 A | 10/1995 | McLeod |
| 5,514,091 A | 5/1996 | Yoon |
| 5,522,827 A | 6/1996 | Combs |
| 5,536,270 A | 7/1996 | Songer |
| 5,541,380 A | 7/1996 | Ogden |
| 5,568,865 A | 10/1996 | Mase |
| 5,569,253 A | 10/1996 | Farris |
| 5,578,057 A | 11/1996 | Wenstrom |
| 5,649,927 A | 7/1997 | Kilpela |
| 5,660,091 A | 8/1997 | Stone |
| 5,702,399 A | 12/1997 | Kilpela |
| 5,752,959 A | 5/1998 | Korhonen |
| 5,755,704 A | 5/1998 | Lunn |
| 5,810,825 A | 9/1998 | Huebner |
| 5,849,012 A | 12/1998 | Abboudi |
| 5,902,305 A | 5/1999 | Beger |
| 5,908,421 A | 6/1999 | Beger |
| 5,935,130 A | 8/1999 | Kilpela |
| 5,935,133 A | 8/1999 | Wagner |
| 5,941,881 A | 8/1999 | Barnes |
| 6,017,347 A | 1/2000 | Huebner |
| 6,077,268 A | 6/2000 | Farris |
| 6,086,590 A | 7/2000 | Margulies |
| 6,099,527 A | 8/2000 | Hochschuler |
| 6,120,506 A | 9/2000 | Kohrs |
| 6,123,709 A | 9/2000 | Jones |
| 6,277,120 B1 | 8/2001 | Lawson |
| 6,342,068 B1 | 1/2002 | Thompson |
| 6,378,289 B1 | 4/2002 | Trudeau |
| 6,387,099 B1 | 5/2002 | Lange |
| 6,398,787 B1 | 6/2002 | Itoman |
| 6,399,886 B1 | 6/2002 | Avellanet |
| 6,454,770 B1 | 9/2002 | Klaue |
| 6,475,220 B1 | 11/2002 | Whiteside |
| 6,494,907 B1 | 12/2002 | Bulver |
| 6,520,965 B2 | 2/2003 | Chervitz |
| 6,575,913 B1 | 6/2003 | Woolley |
| 6,605,091 B1 | 8/2003 | Iwanski |
| 6,629,975 B1 | 10/2003 | Kilpela |
| 6,730,091 B1 | 5/2004 | Pfefferle |
| 6,832,532 B2 | 12/2004 | Kilpela |
| 6,872,210 B2 | 3/2005 | Hearn |
| 7,052,499 B2 | 5/2006 | Steger |
| 7,156,847 B2 | 1/2007 | Abramson |
| 7,207,993 B1 | 4/2007 | Baldwin |
| 7,229,444 B2 | 6/2007 | Boyd |
| 7,250,054 B2 | 7/2007 | Allen |
| 7,494,461 B2 | 2/2009 | Wells |
| 7,635,365 B2 | 12/2009 | Ellis |
| 7,695,501 B2 | 4/2010 | Ellis |
| 7,785,355 B2 | 8/2010 | Mohr |
| 7,803,176 B2 | 9/2010 | Teague |
| 8,282,675 B2 | 10/2012 | Maguire |
| 8,298,247 B2 | 10/2012 | Sterrett |
| 8,313,517 B2 | 11/2012 | Mohr |
| 8,337,497 B2 | 12/2012 | Deslauriers |
| 8,372,123 B2 | 2/2013 | SmissonIII |
| 8,460,295 B2 | 6/2013 | McClellan |
| 8,460,345 B2 | 6/2013 | Steger |
| 8,783,671 B2 | 7/2014 | Ranieri |
| 8,840,735 B2 | 9/2014 | Schaffer |
| 8,984,720 B2 | 3/2015 | Gephart |
| 9,265,543 B2 | 2/2016 | Gephart |
| 9,333,021 B2 | 5/2016 | Gephart |
| 9,510,822 B2 | 12/2016 | Dell'Oca |
| 9,510,882 B2 | 12/2016 | Dell'Oca |
| 9,561,064 B2 | 2/2017 | Goodwin |
| 2002/0072753 A1 | 6/2002 | Cohen |
| 2002/0177861 A1 | 11/2002 | Sugiyama |
| 2003/0153947 A1 | 8/2003 | Koseki |
| 2004/0138666 A1 | 7/2004 | Molz |
| 2004/0199169 A1 | 10/2004 | Koons |
| 2005/0171547 A1 | 8/2005 | Aram |
| 2005/0177179 A1 | 8/2005 | Baynham |
| 2006/0089646 A1 | 4/2006 | Bonutti |
| 2006/0155328 A1 | 7/2006 | Foerster |
| 2006/0167464 A1 | 7/2006 | Allen |
| 2006/0271060 A1 | 11/2006 | Gordon |
| 2006/0287653 A1 | 12/2006 | Rhyne |
| 2007/0225715 A1 | 9/2007 | Deffenbaugh |
| 2008/0195145 A1 | 8/2008 | Bonutti |
| 2008/0275477 A1 | 11/2008 | Sterrett |
| 2008/0287951 A1 | 11/2008 | Stoneburner |
| 2008/0306553 A1 | 12/2008 | Zucherman |
| 2009/0043316 A1 | 2/2009 | Durgin |
| 2009/0054933 A1 | 2/2009 | Mickiewicz |
| 2009/0069812 A1 | 3/2009 | Gillard |
| 2009/0069851 A1 | 3/2009 | Gillard |
| 2009/0105717 A1 | 4/2009 | Bluechel |
| 2009/0171402 A1 | 7/2009 | DellOca |
| 2010/0042106 A1 | 2/2010 | Bryant |
| 2010/0057091 A1 | 3/2010 | Oosterom |
| 2010/0094294 A1 | 4/2010 | Gillard |
| 2010/0094362 A1 | 4/2010 | Lutze |
| 2010/0121387 A1 | 5/2010 | Belliard |
| 2010/0179595 A1 | 7/2010 | Jackson |
| 2010/0256612 A1* | 10/2010 | Dell'Oca ............... A61B 17/82 606/1 |
| 2010/0305571 A1 | 12/2010 | Pratt |
| 2010/0318137 A1 | 12/2010 | Stucki |
| 2010/0331844 A1 | 12/2010 | Ellis |
| 2010/0331892 A1 | 12/2010 | Fell |
| 2011/0079315 A1 | 4/2011 | Norton |
| 2011/0112537 A1 | 5/2011 | Bernstein |
| 2011/0218580 A1 | 9/2011 | Schwager |
| 2011/0224676 A1 | 9/2011 | Dell'Oca |
| 2011/0319978 A1 | 12/2011 | Schaffer |
| 2012/0016384 A1 | 1/2012 | Wilke |
| 2012/0089193 A1 | 4/2012 | Stone |
| 2012/0215224 A1 | 8/2012 | Songer |
| 2012/0226321 A1 | 9/2012 | Gonzalez-Hernandez |
| 2012/0303065 A1 | 11/2012 | Larroque-Lahitette |
| 2013/0116736 A1 | 5/2013 | de Oliveira |
| 2013/0167334 A1 | 7/2013 | Gephart |
| 2013/0289564 A1 | 10/2013 | Bernstein |
| 2013/0331897 A1 | 12/2013 | Holt |
| 2014/0058445 A1 | 2/2014 | Mattchen |
| 2014/0088688 A1 | 3/2014 | Lilburn |
| 2014/0142638 A1* | 5/2014 | Goodwin ............. A61B 17/842 606/281 |
| 2015/0038969 A1* | 2/2015 | Garcia .................. A61B 17/82 606/74 |
| 2015/0127003 A1 | 5/2015 | Songer |
| 2015/0182674 A1 | 7/2015 | Schaffer |
| 2015/0313656 A1 | 11/2015 | Hulliger |
| 2015/0342654 A1 | 12/2015 | Gephart |
| 2016/0174997 A1 | 6/2016 | Spitznagel |
| 2016/0331431 A1 | 11/2016 | Gephart |
| 2017/0071648 A1 | 3/2017 | Dell'Oca |
| 2017/0156779 A1 | 6/2017 | Bryant et al. |
| 2018/0029824 A1 | 2/2018 | Gephart |
| 2019/0015142 A1 | 1/2019 | Mitchell |

FOREIGN PATENT DOCUMENTS

| | | |
|---|---|---|
| DE | 7707950 U1 | 4/1978 |
| TW | 314764 | 9/1997 |
| WO | 9400063 | 1/1994 |
| WO | 9428812 | 12/1994 |
| WO | 0149191 | 7/2001 |

(56) References Cited

FOREIGN PATENT DOCUMENTS

| WO | 200149191 | 7/2001 |
|---|---|---|
| WO | 0234120 | 5/2002 |
| WO | 2006088452 | 8/2006 |
| WO | 2011041624 | 4/2011 |
| WO | 2011116364 | 9/2011 |
| WO | 2013003719 | 1/2013 |
| WO | 2014140100 A2 | 9/2014 |
| WO | 2017127692 A1 | 7/2017 |
| WO | PCTUS201714355 | 11/2017 |

OTHER PUBLICATIONS

International Search Report and Written Opinion of International Patent Application No. PCT/US17/14355, dated Apr. 14, 2017, 12 pages.
U.S. Appl. No. 62/368,753, filed Jul. 29, 2016, Matthew P. Gephart.
U.S. Appl. No. 62/286,062, filed Jan. 22, 2016, Robert A. Mitchell.
U.S. Appl. No. 15/422,109, filed Feb. 1, 2017, Robert Goodwin.
Acute Innovation-Quick and Easy Installation & Re-entry, Acute Innovation, LLC, htto://www.acuteinnovations.com/oroducts/AcuTie/Installtion, May 16, 2012, 7 pages.
Ease of Wire with the Stability of a Plate, AcuTie Sternal Closure System, Oct. 2010, 12 pages.
Re-Entry Options, AcuTie Sternal Closure System, accessed May 16, 2012, 1 page.
SternaLock Blu Primary Closure System, Biomet Microfixation, Form No. BMF00-3265, Rev 05k1110, 2011, 10 pages.
Technique Guide, Modular Sternal Cable System Flexibility and Strength in Sternal Closure and Repair, Synthes CMF, Jul. 2008, 39 pages.
Technique Guide, Titanium Sternal Fixation System for Stable Internal Fixation of the Sternum, Synthes, Inc., Oct. 2010, 36 pages.
Extended European Search Report and Search Opinion dated Aug. 21, 2019, in corresponding European Patent Application No. 17742033.8, 8 pages.

\* cited by examiner

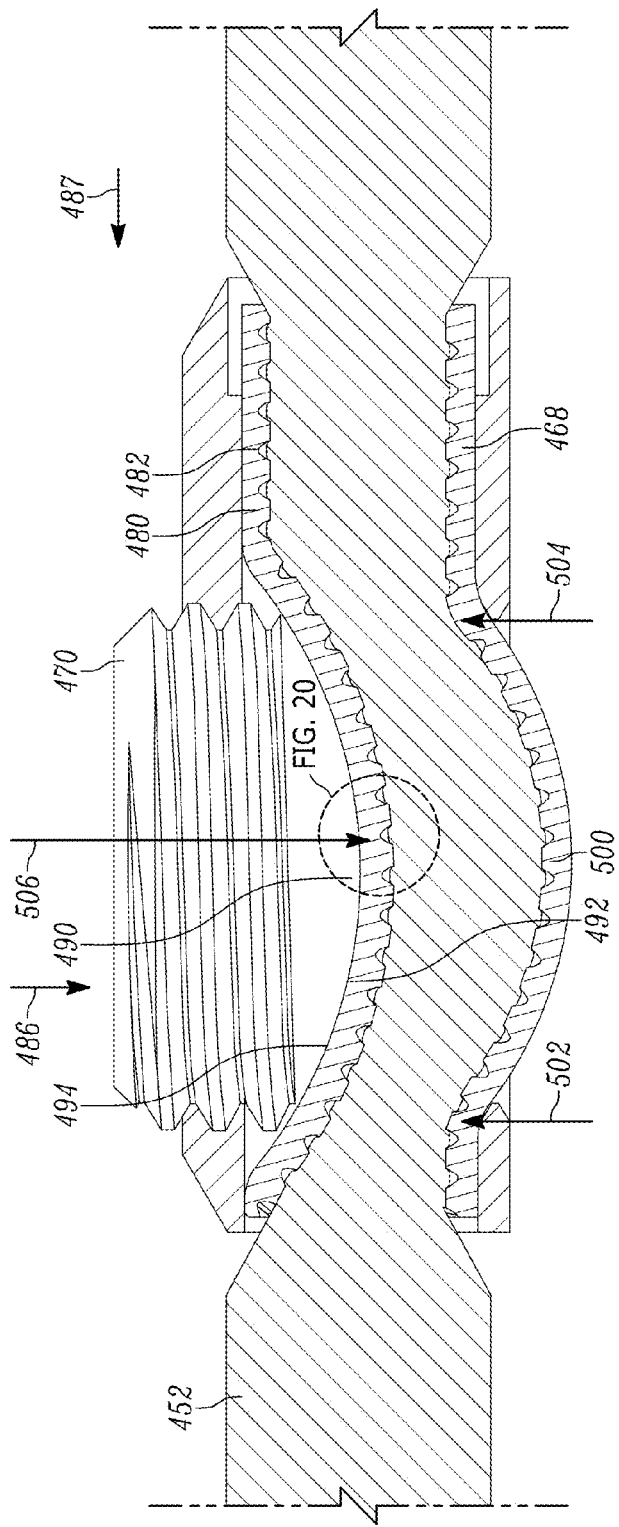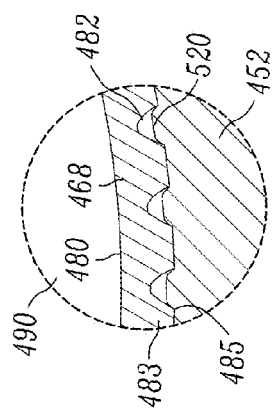
FIG. 19
FIG. 20

BONE PLATE HAVING A CONNECTOR AND A CONNECTOR FOR A SURGICAL LOOP

CROSS-REFERENCE TO RELATED APPLICATION

This application claims the benefit of U.S. Provisional Patent Application No. 62/286,145, filed Jan. 22, 2016, which is hereby incorporated by reference in its entirety.

FIELD

The invention relates to devices for stabilizing bones and, more specifically, to bone plates and surgical loops having elongate, flexible members for extending around the bones.

BACKGROUND

Surgical loops are used in a variety of surgical procedures to stabilize bones such as those in the spine, hip, and sternal areas of the body. Surgical loops often utilize an elongate flexible member, such as a single strand wire or a cable, and a crimp for securing the wire or cable. For example during a surgical procedure, one end of a cable is secured to the crimp and the other end of the cable is advanced around bone portions, through the crimp, and tensioned. The crimp is deformed to lock the crimp to the cable and hold the tension in the cable. In some applications, the bone portions may be relatively soft due to disease or the type of bone such that tension applied to the cable causes the cable to partially sink into the bone portions.

SUMMARY

In accordance with one aspect of the present disclosure, an apparatus for securing bone portions is provided. The apparatus includes a surgical cable having a plurality of elongate elements and a connector having a body. The connector includes a deformable sleeve associated with the body, the deformable sleeve having a through opening for receiving the surgical cable. The through opening has a non-deformed configuration sized to compress the elements of the surgical cable together with the surgical cable extending in the sleeve through opening. The connector further includes an actuator connected to the body that is operable to deform the sleeve and further compress the compressed elements of the surgical cable therein to secure the surgical cable relative to the body. In this manner, the connector may secure the surgical cable to the connector despite the surgical cable being difficult to secure using conventional crimp devices, such as if the elements of the surgical cable are loosely woven.

In one form, the deformable sleeve compresses the surgical cable as the surgical cable is advanced into the through opening from a free state configuration to a near solid state configuration. The deformable sleeve thereby automatically compresses the elements of the surgical cable so that the elements are ready for crimping as the surgical cable is advanced through the deformable sleeve and without requiring additional manipulation by the user. The surgical cable may have an effective outer diameter and the through opening of the deformable sleeve may have an inner diameter smaller than the effective outer diameter of the surgical cable to compress the elements of the surgical cable as the surgical cable is advanced through the deformable sleeve.

The present disclosure also provides an apparatus for securing bone portions that includes a surgical cable and a connector. The connector includes a body, a deformable sleeve associated with the body and having a through opening for receiving a surgical cable, and an actuator connected to the body. The actuator has a lower portion adapted to be shifted in a longitudinal direction between unlocked and locked positions to contact the deformable sleeve and deform the surgical cable extending therein. The body includes sleeve support portions supporting the deformable sleeve that are laterally spaced from the actuator lower portion. The sleeve support portions permit the actuator lower portion to bend the deformable sleeve and the surgical cable therein into lateral spaces between the sleeve support portions and the actuator lower portion as the actuator is shifted in the longitudinal direction. This bending of the deformable sleeve and the surgical cable therein into the lateral spaces creates a tortuous path for the surgical cable through the deformable sleeve which imparts a shape, the shape being similar to a square wave, to the deformable sleeve and the surgical cable. This resists pull-through of the surgical cable from the deformable sleeve because the deformable sleeve and surgical cable would have to straighten out from the imposed shape before the surgical cable can slide lengthwise within the deformable sleeve.

In one form, the actuator lower portion includes a recess adapted to permit a portion of the deformable sleeve to deform into the recess as the actuator lower portion shifts between the unlocked and locked positions thereof. The presence of the recess reduces the surface area of the actuator lower portion that contacts the deformable sleeve. By reducing this contact area, the force the actuator lower portion applies to the deformable sleeve is concentrated to produce an abrupt change in the shape of the sleeve at the areas where the actuator lower portion contacts the sleeve.

In accordance with another aspect of the present disclosure, a method of securing bone portions is provided. The method includes positioning a surgical cable about bone portions and advancing the surgical cable through a connector. The method includes compressing elements of the surgical cable together as the surgical cable is advanced into the connector and securing the surgical cable to the connector.

In one form, advancing the surgical cable through the connector includes advancing the surgical cable into a sleeve of the connector and securing the surgical cable to the connector includes shifting a lower portion of the actuator in a longitudinal direction and deforming the sleeve and surgical cable therein into lateral spaces between the actuator lower portion and sleeve supporting portions of the connector. The deforming of the sleeve and surgical cable into the lateral spaces between the actuator lower portion and the sleeve supporting portions creates neckdown portions in the deformable sleeve and crimps the deformable sleeve to the surgical cable at two spaced positions along the surgical cable.

BRIEF DESCRIPTION OF THE DRAWINGS

FIG. 19 is a cross-sectional view similar to FIG. 18 showing a set screw of the connector in a locked position which deforms the sleeve and creates an interlock between the sleeve inner wall portions and the cable;

FIG. 20 is an enlarged view of the circled area in FIG. 19 showing portions of the cable bulging radially outward into the inner grooves of the sleeve;

DETAILED DESCRIPTION

Figure 1:
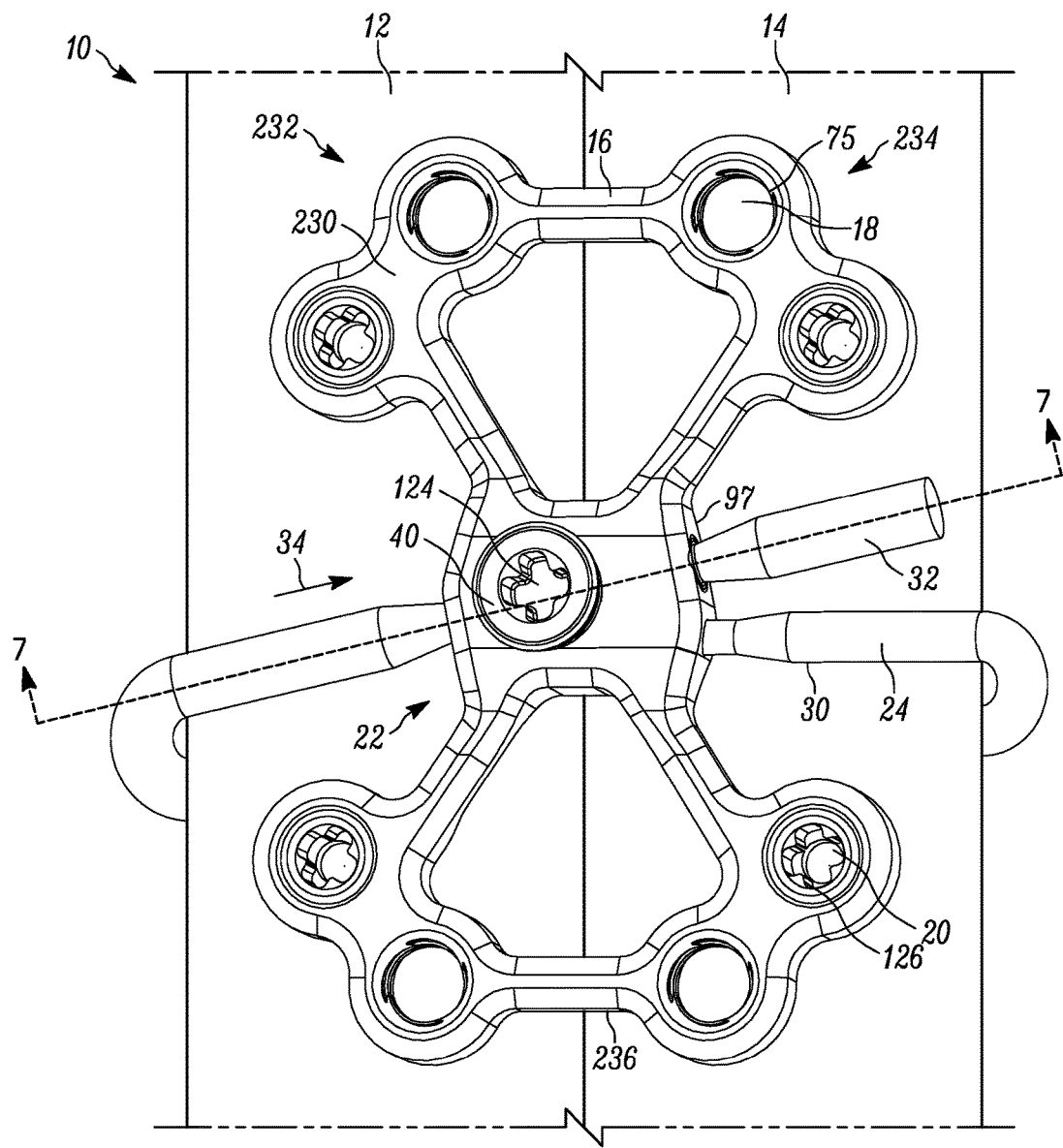
FIG. 1 is a perspective view of a bone plate system including a bone plate having a connector and a surgical cable looped around bone portions.

With reference to FIG. 1, a bone plate system 10 is provided for securing bone portions 12, 14 relative to each other. The bone plate system 10 includes a bone plate 16 having through bores 18 for receiving bone anchors, such as bone screws 20, which are driven into the bone portions 12, 14. The bone plate system 10 includes a surgical cable 24 for being looped around the bone portions 12, 14 and a connector 22 for securing the surgical cable 24 around the bone portions 12, 14. The surgical cable 24 has a trailing end portion 30 for being connected to the connector 22 and a leading end portion 32 that is looped around the bone portions 12, 14. To secure the bone portions 12, 14 using the bone plate system 10, the bone plate 16 is positioned on the bone portions 12, 14 and the leading end portion 32 is looped around the bone portions 12, 14 and is advanced in direction 34 through a deformable sleeve 36 (see FIGS. 2A-C) of the connector 22. The leading end portion 32 is further advanced in direction 34 away from the bone plate 16 to tension the surgical cable 24. An actuator, such as a set screw 40, of the connector 22 is driven from an unlocked to a locked position which deforms the sleeve 36 and secures the tensioned cable 24 relative to the bone plate 16. The bone screws 20 are driven into the bone plate through bores 18 and into the bone portions 12, 14 before or after securing the surgical cable 24 to the bone plate 16. The bone plate system 10 thereby secures the bone portions 12, 14 relative to each other using the rigid fixation provided by the rigid construct of the bone plate 16 and bone screws 20 as well as the compressive force applied by the tensioned surgical cable 24.

The surgical cable 24 may be loosely woven as discussed below and may elongate axially and flatten out against the bone portions 12, 14 as the surgical cable 24 is tensioned. For example, the surgical cable 24 may have a circular cross section and effective diameter of 0.18 inches at rest and the tensioned surgical cable 24 may flatten out against bone to an elliptical cross section having a minor diameter of 0.13 inches. It may therefore be difficult to grasp the surgical cable 24 using conventional crimp devices. In one aspect, the connector 22 addresses this difficulty by compressing the surgical cable 24 from a tubular, free state configuration (see FIG. 5) to a bundled, near solid-state configuration (see FIG. 6) as the surgical cable 24 is advanced into the sleeve through opening 60 which is in a non-deformed configuration. When the set screw 40 is shifted to the locked position, the set screw 40 deforms the sleeve through opening 60 to a deformed configuration with the near solid state configuration surgical cable 24 therein to fix the surgical cable 24 to the connector 22. Because the surgical cable 24 is in its near solid state configuration within the deformable sleeve 36, the sleeve 36 can engage the solid bundle of elements 80 of the surgical cable 24 more firmly than if the elements 80 were free to shift relative to each other within the deformable sleeve 36.

Figure 2A:
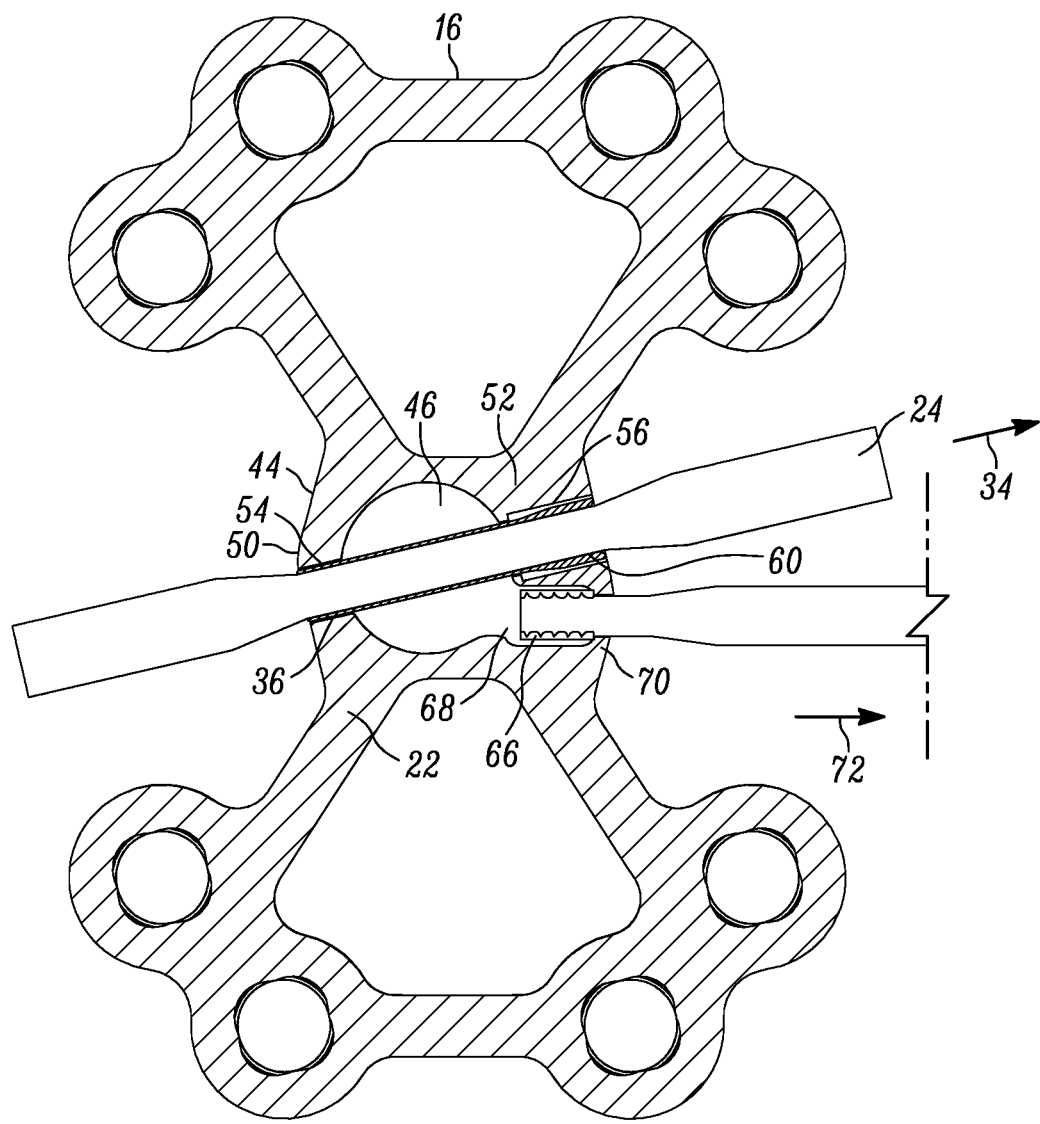
FIG. 2A is a cross-sectional view of the bone plate of FIG. 1 showing a deformable sleeve of the connector extending across a through bore of the connector.

With reference to FIG. 2A, the connector 22 of the bone plate 16 has a body 44 with a bore therein, such as a through bore 46, which receives the set screw 40. The through bore 46 extends along a central, longitudinal axis 48 (see FIG. 7) of the body 44. The body 44 includes sleeve supporting portions 50, 52 that define openings 54, 56 through which the sleeve 36 extends. The deformable sleeve 36 thereby extends across the through bore 46 transverse to the longitudinal axis 48 of the through bore 46. In one approach, the sleeve 36 has a through opening 60 extending along a straight, central axis 62 (see FIG. 2C) that extends perpendicular to the longitudinal axis 48 of the through bore 46.

With reference to FIG. 2A, the surgical cable 24 may have a monofilament or multifilament construction and may include a plug 66 secured to the filament(s) of the surgical cable 24 such as by swaging. The connector body 44 includes a cavity 68 that receives the plug 66 and a collar 70 which resists pull-through of the plug 66 in direction 72. The engagement between the plug 66 and the collar 70 holds the end portion 30 of the surgical cable 24 relative to the bone plate 16 upon tensioning of the surgical cable 24. In another form, the surgical cable may be a medical grade rope.

Figure 2B:
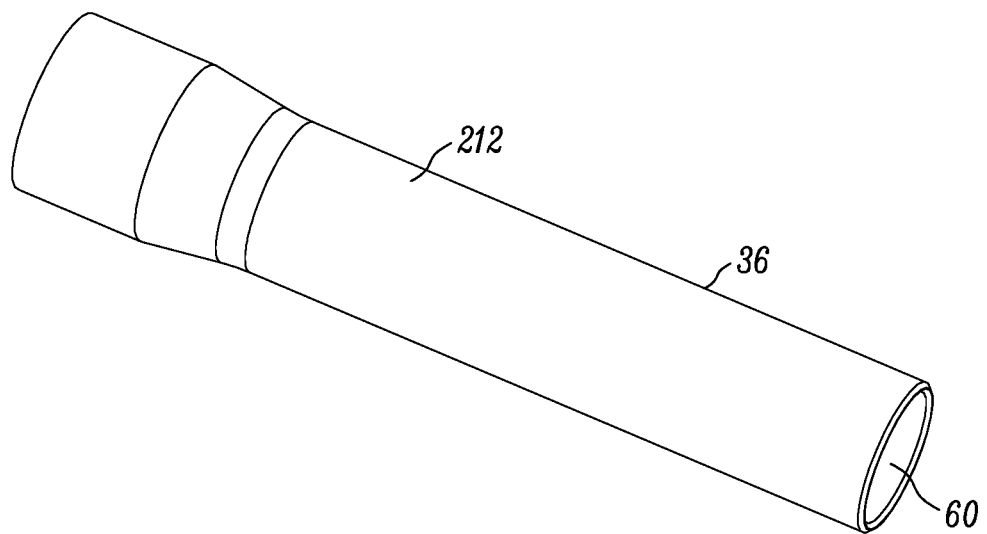
FIG. 2B is a perspective view of the deformable sleeve of FIG. 2A.
Figure 2C:
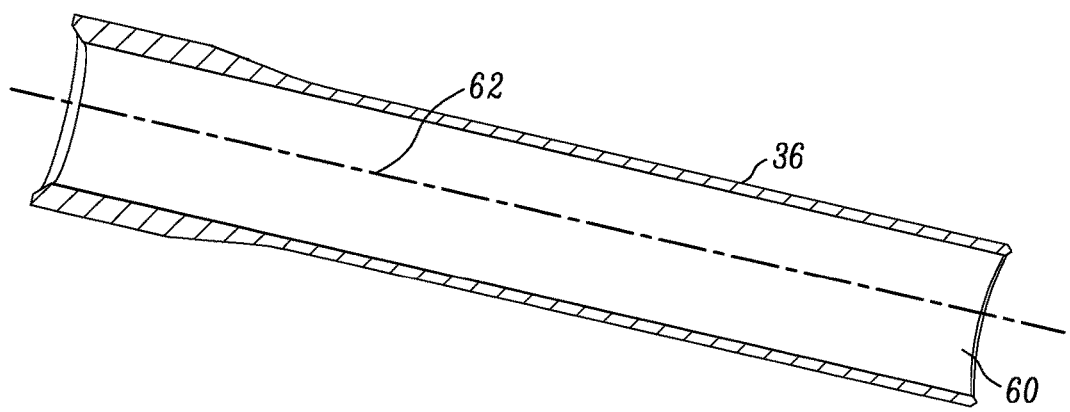
FIG. 2C is a cross-sectional view of the deformable sleeve of FIG. 2B showing a through opening of the deformable sleeve.
Figure 2D:
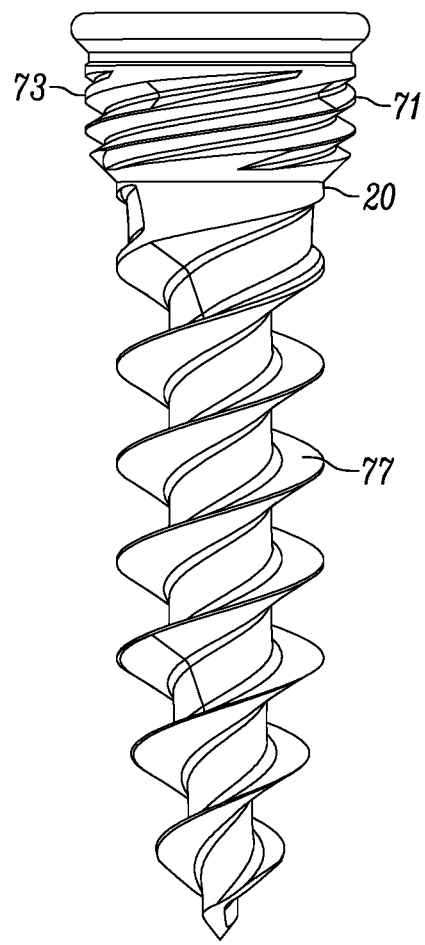
FIG. 2D is an elevational view of a bone screw of the bone plate system of FIG. 1 showing a threaded head portion and a threaded shank portion of the bone screw.

Turning to FIGS. 1 and 2D, the bone screws 20 include a head portion 71 with a rotary drive structure, such as socket 126, for engaging a driving tool. The set screw 40 has a rotary drive structure, such as a socket 124, for engaging a locking tool. In one form, the sockets 124, 126 are similar so that the same tool may be used to both drive the bone screws 20 and the lock set screw 70. The head portion 71 may also include threads 73 that engage corresponding threads 75 of the bone plate throughbores 18 to resist back-out of the bone screws 20. The bone screws 20 also include a shank portion 77 with threads for engaging the bone portions 12, 14.

Figure 3:
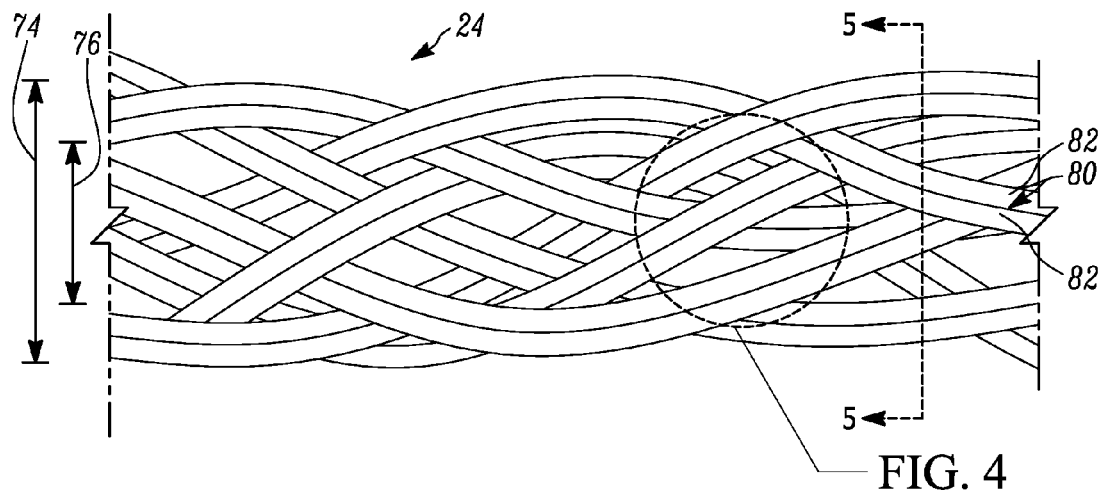
FIG. 3 is an elevational view of the surgical cable of FIG. 1 showing woven elements of the surgical cable.
Figure 4:
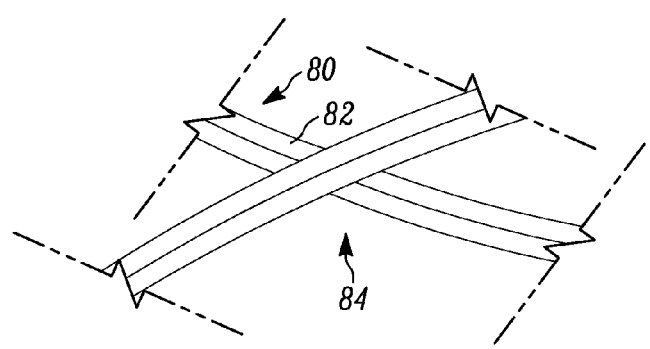
FIG. 4 is an enlarged view of the circled area in FIG. 3 showing elements of the surgical cable made up of individual strands.

With reference to FIG. 3, the surgical cable 24 may be tubular and have an outer diameter 74 and an inner diameter 76. The hollow surgical cable 24 may include a plurality of elements 80 that each include a plurality of strands 82. Each strand 82 may be wound around a mandrel during production to form a helix and the elements 80 are woven together so that an overlapping pattern of crisscrossing helixes is formed by the elements 80 to create the surgical cable 24. The crisscrossing elements 80 intersect at junctions 84, as shown in FIG. 4.

Figure 5:
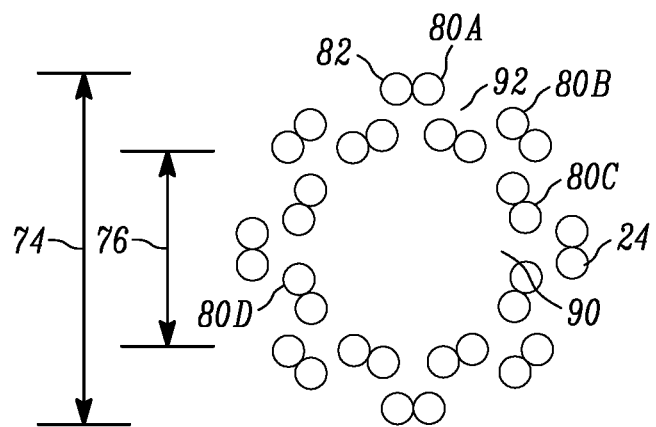
FIG. 5 is a cross-sectional view of the surgical cable taken across line 5-5 in FIG. 3 showing that the surgical cable has sixteen elements each having two strands, the surgical cable being in a tubular, free state configuration with gaps between the elements and the elements defining an inner diameter of the cable.

The number and arrangement of elements 80 and strands 82 may be selected for a particular application. With reference to FIG. 5, the surgical cable 24 shown includes sixteen elements 80 that each include two strands 82. The elements 80 define an interior 90 of the surgical cable 24 having the inner diameter 76. The inner diameter 76 may be measured between elements 80C, 80D across the interior 90.

The number and arrangement of elements 80 and strands 82 may be selected for a given outer diameter 74 of the surgical cable 24. For example, 4, 8, 64, or 128 of the elements 80 may be used with a larger number of elements 80 providing a denser weave and a smaller number of elements 80 providing a looser or more sparse weave. Further, the number of strands 82 in each element 80 may be selected for a particular application, such as 2, 3, 7, 19, and 133 of the strands 82. In one approach, the diameter of the individual strands 82 increases as the number of strands 82 decreases.

With reference to FIG. 5, the surgical cable 24 has a free state configuration wherein there are gaps 92 between elements 80. The surgical cable 24 has the free state configuration when there are no operative forces acting on the surgical cable 24 (e.g., tension), such as if the surgical cable 24 were resting on a work bench. In the free state configuration, the surgical cable 24 has the diameter 74 which may be considered the effective diameter of the surgical cable 24.

Figure 6:
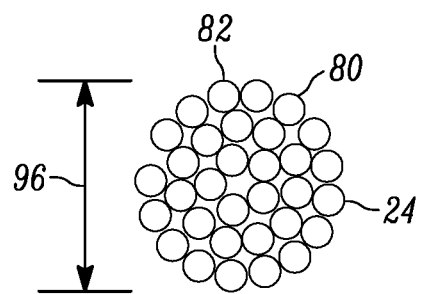
FIG. 6 is a cross-sectional view similar to FIG. 5 showing the surgical cable in a bundled, near-solid state configuration wherein the elements are held tightly together.

The elements 80 are loosely woven, and may be compressed together to remove the gaps 92. With reference to FIG. 6, the surgical cable 24 has a near solid-state configuration wherein the elements 80 contact one another and the gaps 92 have been reduced. The interior 90 of the surgical cable 24 is substantially collapsed with the surgical cable 24 in the near solid state configuration such that the elements 80 are tightly bundled together. As used herein, the term solid state configuration refers to the elements 80 being sufficiently compressed together so that the surgical cable 24 can pass though the smallest ring gauge the surgical cable 24 can fit through. In the solid state configuration, the surgical cable 24 may have a non-circular cross section. By nearly solid state configuration, it is meant that the surgical 24 is expanded slightly from the solid state configuration. For example, the surgical cable 24 may haven effective diameter of 0.105 inches in the free state, an outer diameter of 0.054 inches in the solid state, and the sleeve opening 60 has a diameter of 0.0625 inches. The sleeve 36 compresses the surgical cable 24 to the nearly solid state configuration, rather than the solid state configuration, so that the surgical cable 24 can easily slide within the sleeve 36. In one form, the diameter of the sleeve through opening 60 may be 75 percent or less, 70 percent or less, 65 percent or less, 60 percent or less, 55 percent or less, or 50 percent or less the effective outer diameter of the free state surgical cable 24.

In the near solid state configuration, there may be some small air gaps between the strands 82 of the elements 80, however, majority of the elements 80 will be in contact with other elements 80. When the cable 24 is in the near solid state configuration, the outer diameter 96 (see FIG. 6) is smaller than the outer diameter 74 (see FIG. 5) when the surgical cable 24 is in the free state configuration. The near solid state diameter 96 may be in the range of approximately 0.04 inches to approximately 0.07 inches, such as approximately 0.54 inches or 0.06 inches; the free state diameter 74 may be in the range of approximately 0.8 inches to approximately 0.2 inches, such as approximately 0.105 or 0.18 inches. The near solid state outer diameter 96 may be a fraction of the free state outer diameter 74, such as less than three quarters, less than three-fifths, or less than half of the free state outer diameter 74. For comparison, the strands 82 may each be monolithic wires having a diameter in the range of approximately 0.001 inches to approximately 0.003 inches, such as approximately 0.002 inches.

Figure 7:
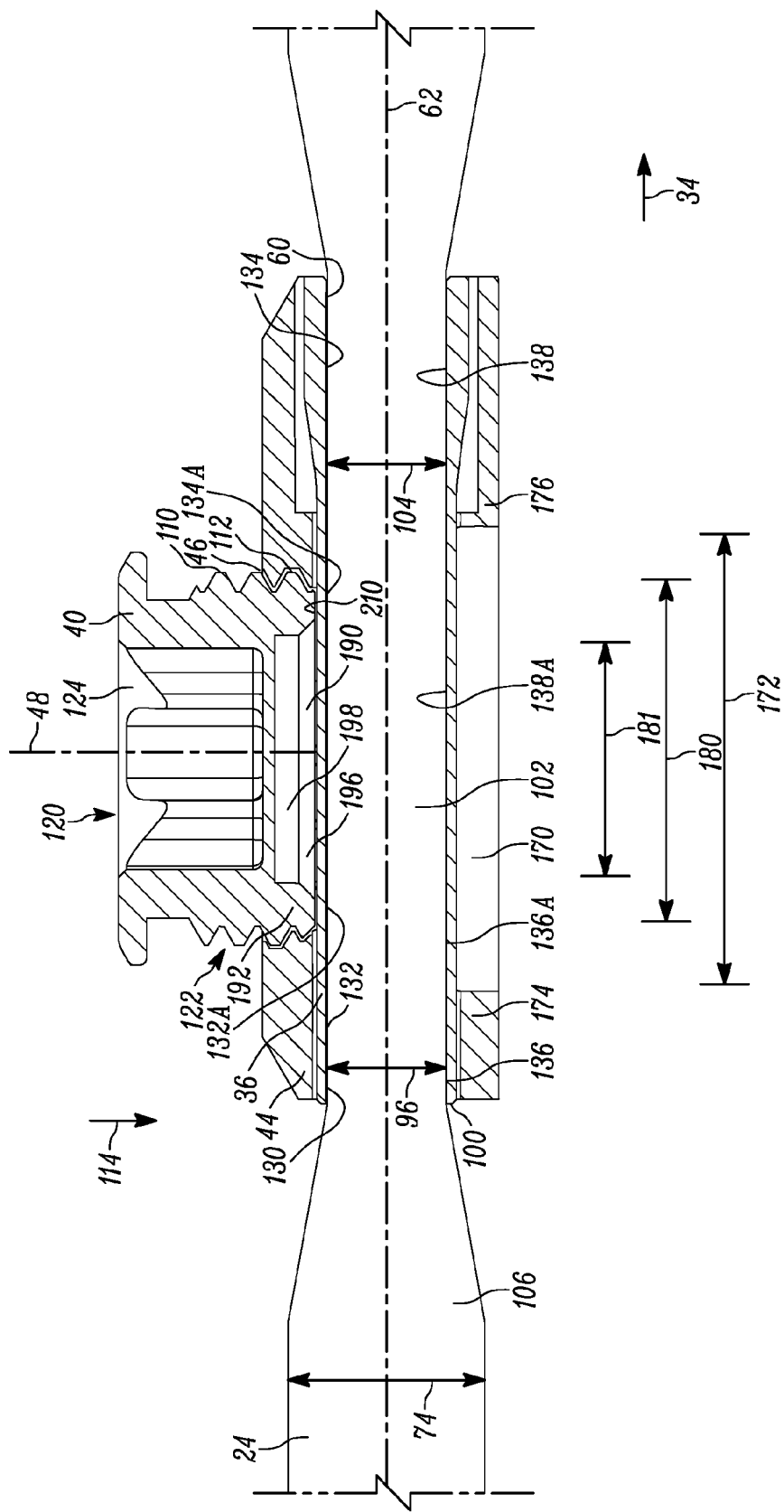
FIG. 7 is a cross-sectional view taken across line 7-7 in FIG. 1 showing a set screw of the connector in a proud, unlocked position and the sleeve through opening in an non-deformed configuration.

With reference to FIG. 7, the sleeve 36 has at least one surface 100 that constricts the surgical cable 24 as the surgical cable 24 is advanced in direction 34 into the through opening 60 of the sleeve 36. The through opening 60 of the sleeve 36 has an inner diameter 104 selected to compress the elements 80 of the surgical cable 24 from the free state configuration to the near solid state configuration. In this manner, a length 102 of the cable 24 within the sleeve through opening 60 has the near solid state outer diameter 96 while the cable 24 outside of the deformable sleeve 36 may have the free state diameter 74. The through opening 60 may have a non-circular shape, such as elliptical, triangular, or square, which are sized to compress the elements 80 together. The surgical cable 24 has tapered portions 106 connecting the surgical cable length 102 having the near solid-state configuration within the deformable sleeve 36 to the portions of the surgical cable 24 having the free-state configuration outside of the deformable sleeve 36.

The surgical cable 24 may be tensioned by advancing the leading end portion 32 of the surgical cable 24 through a tensioner and positioning the tensioner against a side 97 (see FIG. 1) of the connector body 44. Examples of tensioners may be found in U.S. Patent Application Publication No. 2014/0142638, published May 22, 2014, titled Bone Plate System and Method, which is hereby incorporated by reference in its entirety.

The tensioner may then be used to shift the leading end portion 32 away from the connector body 44, which tensions the surgical cable 24 around the bone portions 12, 14. The surgical cable 24 may slide within the through opening 60 of the deformable sleeve 36 in direction 34 as tension is applied to the surgical cable 24, as shown in FIG. 7. As the surgical cable 24 enters the through opening 60, the deformable sleeve 36 compresses the surgical cable 24 to a near solid state configuration while the surgical cable exiting the through opening 60 may expand from the near solid state configuration. Further, the diameter of the cable 24 outside of the deformable sleeve 36 may decrease during tensioning due to axial elongation of the surgical cable 24, but the diameter 96 of surgical cable 24 in the deformable sleeve 36 remains substantially unchanged because the elements 80 along the length 102 have already been compressed due to the reduced inner diameter of the deformable sleeve 36.

With continued reference to FIG. 7, the set screw 40 is connected to the body 44 by threads 110, 112, that permit turning of the set screw 40 to produce shifting of the set screw 40 in direction 114 along the longitudinal axis 48 to the locked position thereof. The threads 110, 112 also resist shifting of the set screw 40 away from the locked position. The set screw 40 may be connected to the body 44 in a number of ways, such as by a bayonet connection. The set screw 40 includes an upper, tool-receiving portion 120 and a leading, lower portion 122. The tool-receiving portion 120 includes the socket 124 for receiving a driver tool, such as a torque-limiting screw driver. The set screw 40 may have a monolithic construction so that turning the tool receiving portion 120 directly causes turning of the lower portion 122 and shifting of the lower portion 122 along the axis 48. In other approaches, the set screw 40 may have two or more assembled components that are operable to transfer input at the tool receiving portion 120 into advancement of the lower portion 122.

Figure 8:
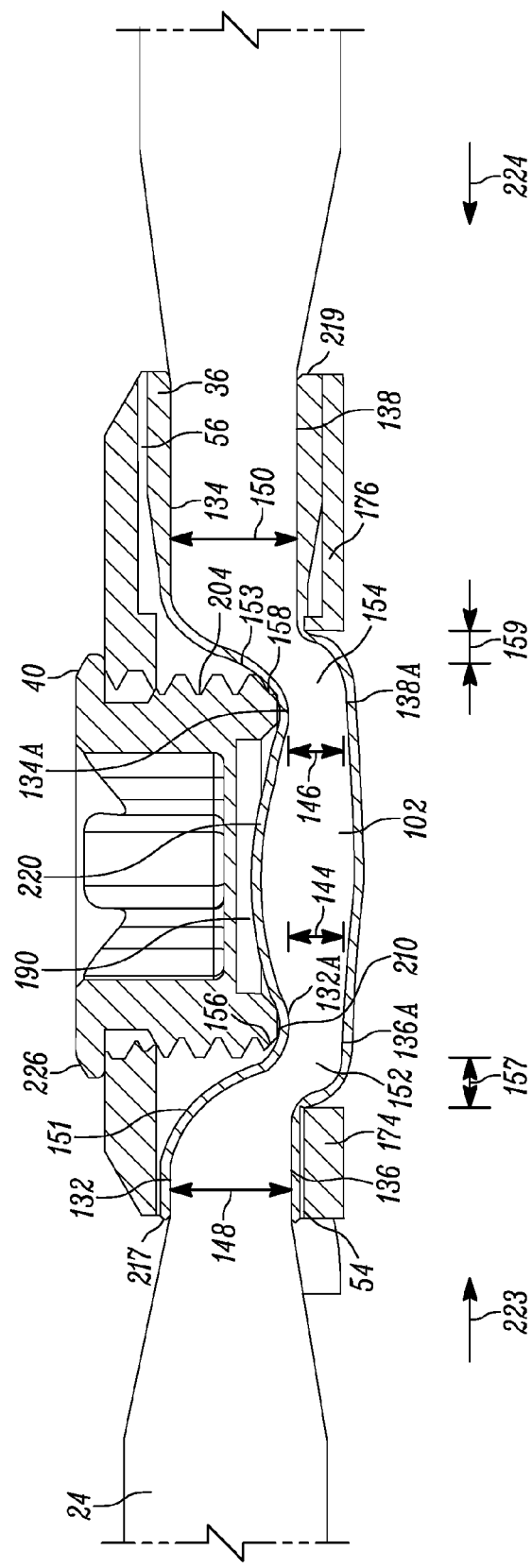
FIG. 8 is a cross-sectional view similar to FIG. 7 showing the set screw driven to a locked position which deforms the deformable sleeve and surgical cable therein and secures the surgical cable to the connector.

With reference to FIGS. 7 and 8, the connector 22 has an unlocked configuration wherein the leading end portion 32 of the surgical cable 24 may be advanced in direction 34 through the through opening 60 of the sleeve 36 and a locked configuration wherein the surgical cable 24 is fixed within the connector 22. With reference to FIG. 7, the sleeve 36 has an inner surface 130 extending about the through opening 60. The sleeve inner surface 130 includes upper surface portions 132, 134 and lower surface portions 136, 138 axially aligned with support portions 174, 176 of the connector body 44. The sleeve inner surface 130 also includes upper surface portions 132A, 134A and lower surface portions 136A, 138A axially below the set screw 40. The pairs of axially aligned upper and lower surface portions 132/136, 132A/136A, 134/138A, and 134/136A are all separated by the inner diameter 104 of the sleeve 36 when the connector 22 is in the unlocked configuration.

Driving the set screw 40 in direction 114 from the unlocked position (FIG. 7) to the locked position (FIG. 8) reconfigures the connector from the unlocked to locked configurations. Driving the set screw 40 in direction 114 to the locked position causes an annular wall 192 of the set screw lower portion 122 to contact the deformable sleeve 36 at the upper surface portions 132A, 134A. The annular wall 192 may have a continuous annular corner extending therearound and corners 156, 158 that contact the deformable sleeve 36 may be diametrically opposed portions of the annular corner of the annular wall 102.

The set screw annular wall 192 urges the deformable sleeve 36 downward at the upper surface portions 132A, 134A. The near solid-state surgical cable length 102 extending through the deformable sleeve 36 transfers this downward shifting of the upper surface portions 132A, 134A into downward shifting of the lower surface portions 136A, 138A. In this manner, driving the set screw 40 to the locked position vertically shifts the upper and lower surface portions 132A, 134A, 136A, 138A of the deformable sleeve 36 downward relative to the upper and lower surface portions 132, 134, 136, 138. This deformation of the sleeve 36 forms neckdown portions 151, 153 in the deformable sleeve 36 and bends 152, 154 in the surgical cable 24 around corners 156, 158 of the set screw 40. This creates a tortuous path for the surgical cable 24 as it extends along the sleeve 36 and imparts a square-wave like shape to the surgical cable. Forcing and holding the surgical cable 24 and sleeve 36 into multiple areas of deformation allows the connector 22 to engage the surgical cable. In another form, the surgical cable 24 and sleeve 36 may be forced and held in a single area of deformation. Further, the set screw 40 may take many shapes, and deflects and holds the surgical cable 24 and sleeve 36 at the location(s) of deformation. The set screw 40 may operate as a pinch style area reduction or a partial shear style clamp caused by the set screw 40 advancing in relation to the support portions 174, 176.

The support portions 174, 176 of the connector body 44 are laterally offset by distances 157, 159 to provide clearance for the sleeve 36 and surgical cable 24 therein to bend around the set screw 40 and through lateral spaces between the set screw lower portion 122 and the support portions 174, 176.

The support portions 174, 176 also apply a reactive upward force on the deformable sleeve 36 at the lower surface portions 136, 138 in response to the downward force applied by the set screw annular wall 192. The opposing upward and downward forces caused by the set screw 40 shifting to the locked position decreases distances 144, 146 between upper and lower surface portions 132A/136A and 134A/138A which crimps the elements 80 of the surgical cable 24 between the upper and lower surface portions 132A/136A and 134A/138A. This crimping creates two pinch points at spaced locations along the surgical cable 24 which fix the surgical cable 24 within the deformable sleeve 36.

With reference to FIGS. 7 and 8, the connector 22 provides a path for the sleeve 36 and the cable 24 to deform around the set screw 40 while providing sufficient support for the sleeve 36 as the sleeve 36 deforms. In one form, the through bore 46 includes an undercut 170 at the lower end thereof that defines a distance, such as a diameter 172, between the support portions 174, 176 of the body 44. The lower portion 122 of the set screw 40 has an outer diameter 180 that is smaller than the diameter 172 to provide clearance for the deformable sleeve 36 and surgical cable 24 therein to deform around the set screw annular wall 192. In this manner, the set screw 40 and support portions 174, 176 thereby act as a forming horn to impart a shape to the surgical cable 24 within the deformable sleeve 36 which resists removal of the surgical cable 24 from the deformable sleeve 36. With reference to FIG. 8, the deformable sleeve 36 has ends 217, 219 that may shift slightly inward in directions 223, 224 as the set screw 40 deforms the sleeve 36 to evenly distribute stresses within the sleeve 36 during the deformation and improves the strength of the locked connector 22.

In one form, the lower portion 122 of the set screw 40 includes a recess 190 for receiving a portion 220 of the deformable sleeve 36 and the annular wall 192 extends around the recess 190. The recess 190 has an inner diameter 181 and the radial thickness of the annular wall 192 is generally defined between the diameters 180, 181. The set screw 40 may include a beveled surface 196 that opens to a chamber 198. In one approach, the chamber 198 may be in communication with the socket 124. The annular wall 192 may define an inner diameter 181 of the chamber 198. In one form, the diameter 172 is in the range of approximately 0.2 inches to approximately 0.25 inches, such as 0.233 inches; the diameter 180 is in the range of approximately 0.16 inches to approximately 0.2 inches, such as 0.173 inches; and the diameter 181 is in the range of approximately 0.1 inches to approximately 0.15 inches, such as 0.125 inches.

With reference to FIGS. 2B and 8, the annular wall 192 has a lower surface 210 that contacts an outer surface 212 of the sleeve 36 and turns relative to the outer surface 212 as the set screw 40 is turned and driven to the locked position. The lower surface 210 may be flat or tapered, as two examples. Due to the presence of the recess 190, the lower surface 210 has less surface area for contacting the sleeve outer surface 212 than if the lower surface 210 were a complete circle. By reducing the surface area of the lower surface 210, the set screw 40 may transmit a greater amount of force to the deformable sleeve 36 for a given torque applied to the set screw 40. In other words, the recess 190 isolates the pressure applied by the set screw 40 against the deformable sleeve 36 to two small surface portions of the annular wall 192 on opposite sides of the recess 190.

As shown in FIG. 8, driving the set screw 40 to the locked position deforms the portion 220 of the sleeve 36 and a portion of the surgical cable 24 therein into the recess 190 of the set screw 40. This results in the portion 220 of the deformable sleeve 36 being indirectly deformed by the set screw 40. The portion 220 has an enlarged cross-section relative to the cross-sections of the deformable sleeve 36 between the upper and lower surface portions 132A/136A and 134A/138A. The cross-section of the surgical cable 24 alternates along the length 102 including the smaller cross-section between surface portions 132A/136A, the larger cross-section at the portion 220, and the smaller cross section between the surface portions 134A/138A. This alternating cross-section of the surgical cable 24 along the length 102 resists sliding movement of the elements 80 relative to each other and further fixes the surgical cable 24 within the deformable sleeve 36.

The connector 22 thereby provides multiple gripping operations for holding the surgical cable 24. First, the connector 22 compresses the cable 24 from a free state to a near solid state configuration as the cable 24 is advanced through the sleeve through opening 60. Second, driving the set screw 40 to the locked position thereof bends the deformable sleeve 36 and near solid-state surgical cable 24 therein around the set screw 40 to impart a tortuous path to the surgical cable 24. Third, the set screw 22 crimps the surgical cable 24 within the deformable sleeve 36 at two locations—between the upper and lower surface portions 132A, 136A and between the upper and lower surface portions 134A, 138A. These three aspects operate together to securely fix the surgical cable 24 relative to the connector 22.

With reference to FIG. 1, the bone plate 16 includes a bone plate body 230 having halves 232, 234 rigidly connected by the connector 22 and elongated supports 236. In one form, the connector body 44 is monolithically formed with the bone plate body 230 as a single piece of material, such as metal or plastic. In other forms, the connector body 44 and the bone plate body 230 may comprise two or more components assembled together.

Figure 9:
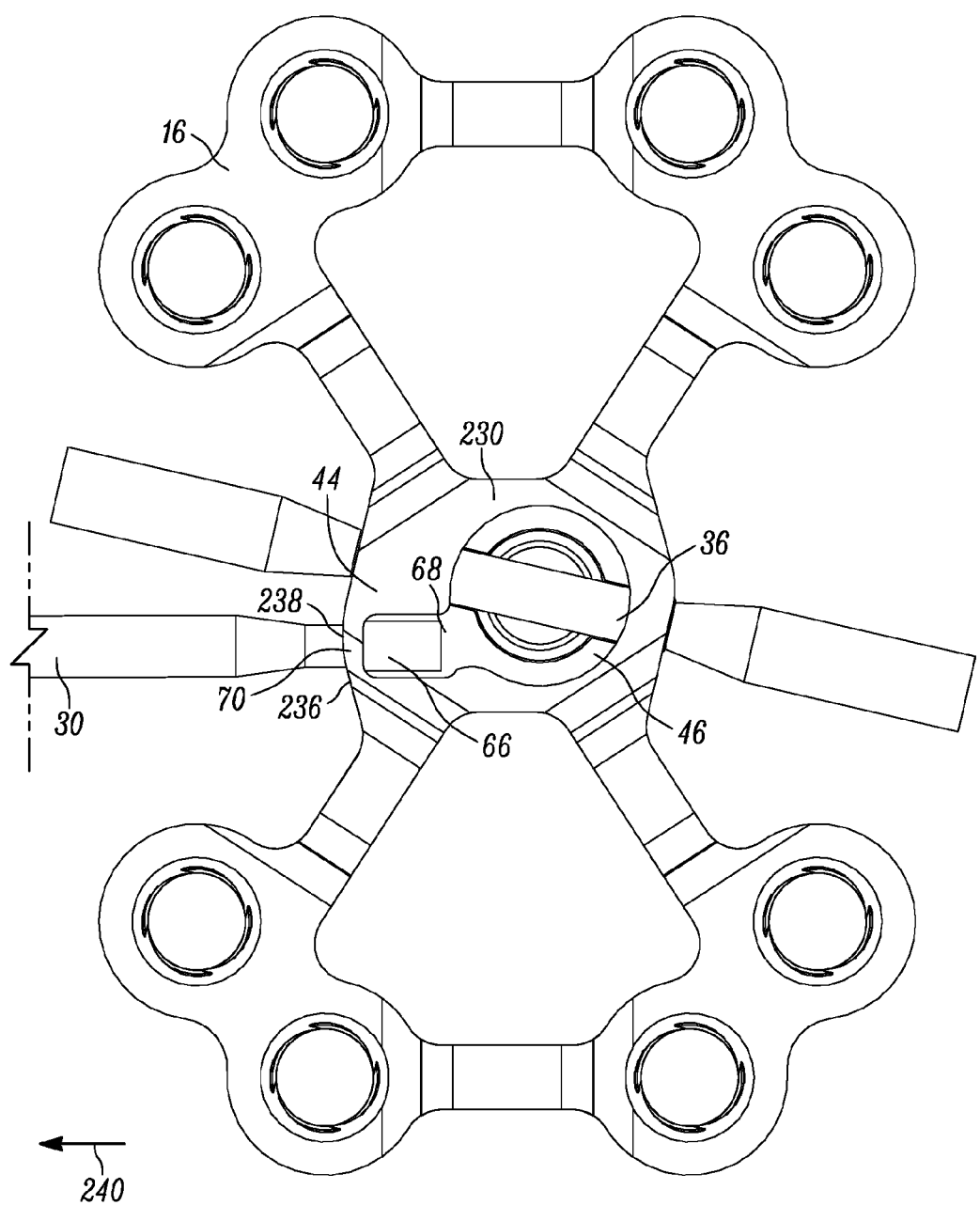
FIG. 9 is a bottom plan view of the bone plate and surgical cable of FIG. 1 showing a recessed pocket on the underside of the bone plate that receives a plug of the surgical cable.

With reference to FIG. 9 the connector body 44 may have a lower surface 234 and the cavity 68 may open to the lower surface 234. The connector body 44 may have a side wall 236 with an opening 238 therein. To connect the trailing end portion 30 of the surgical cable 24 to the bone plate 16, the leading end portion 32 of the surgical cable 24 is advanced into the cavity 68 and through the opening 238 in direction 240. The leading end portion 32 is advanced in direction 240 until the plug 66 is positioned in the cavity 68 and abuts the collar 70.

Figure 10:
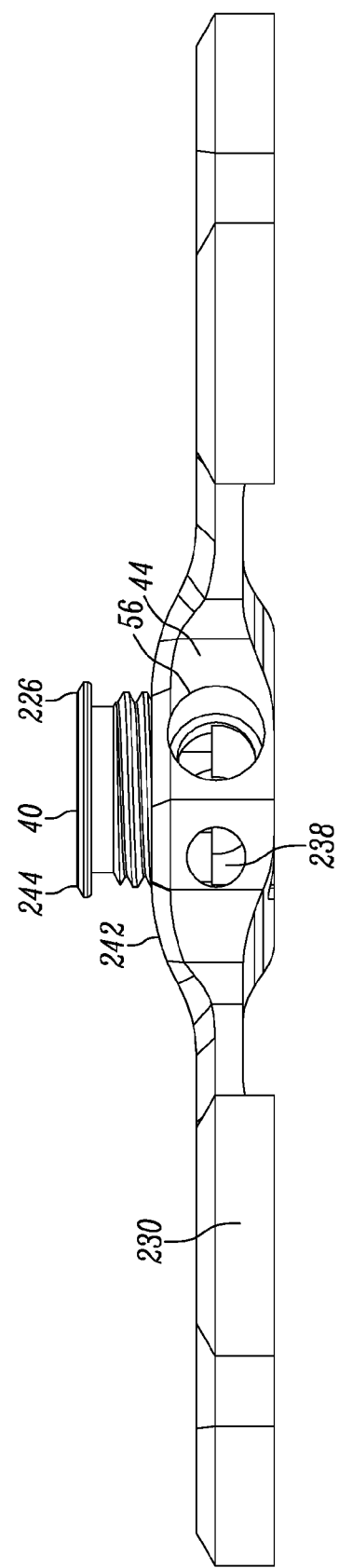
FIG. 10 is an elevational view of the bone plate of FIG. 1 showing openings in the side of the bone plate for receiving the surgical cable.

With reference to FIG. 10, the bone plate 16 is shown with the cable 24 removed therefrom. The connector body 44 has an upper surface 242 and the set screw 40 may be proud of the upper surface 242 when the set screw is in the unlocked positon thereof. Once the set screw 40 is driven to the locked position, an upper surface 244 of the set screw 40 may be flush with or below the upper surface 242 of the connector body 44. In one form, the set screw 40 has a lip 226 that abuts the body upper surface 242 when the set screw 40 has been driven to the locked position thereof to restrict further advancing of the set screw 40 beyond a predetermined position. In this manner, the pressure the set screw 40 applies to the sleeve 36 is controlled by the distance the set screw 40 can travel. In another approach, an instrument used to drive the set screw 40 may have a torque limiting device which controls the amount of pressure the set screw 40 applies to the sleeve 36. At a predetermined torque, the sleeve 36 is displaced enough to where sufficient pull-through resistance is achieved. In this manner, the pressure the set screw 40 applies to the sleeve 36 is controlled by the torque applied to the set screw 40.

A surgical loop is also provided that includes a loosely-woven surgical cable and a connector. The connector has a body configured to receive an end of the cable and a locking mechanism configured to be fixed to another end of the cable. The locking mechanism includes an actuator movable between unlocked and locked positions and a deformable locking member that receives the surgical cable. In the unlocked position of the actuator, the locking member is not deformed and is in an unlocked configuration thereof. Moving the actuator to the locked position causes deformation of the locking member and reconfigures the locking member to a locked configuration. In the locked configuration, the deformed locking member includes a plurality of gripping portions extending transverse to a length of the cable that tightly engage the cable and resist movement of the cable relative to the locking member.

In one form, the locking member includes a sleeve having a though opening that receives the cable. The sleeve has thicker and thinner portions and moving the actuator to the locked position deforms the sleeve. The thinner portions of the sleeve deform more than the thicker portions and cause the sleeve to be bent at a plurality of locations therealong. This forms discrete segments of an inner surface of the sleeve separated by ridges or edges. The ridges or edges extend transversely to the length of the cable and engage the cable to provide pull-through resistance.

In another form, the locking member includes a sleeve having a through opening that receives the cable. The sleeve includes a wall extending around the cable with at least one inner wall portion extending transversely to the length of the cable. Moving the actuator to the locked position deforms the sleeve and causes the sleeve to engage the at least one inner wall portion of the sleeve with the cable. The sleeve may include a plurality of recesses or grooves separating the inner wall portions. Moving the actuator to the locked position deforms the sleeve and forces outer portions of the cable into or against the grooves. The inner wall portions engage the cable and resist the cable from sliding relative to the sleeve.

Figure 11A:
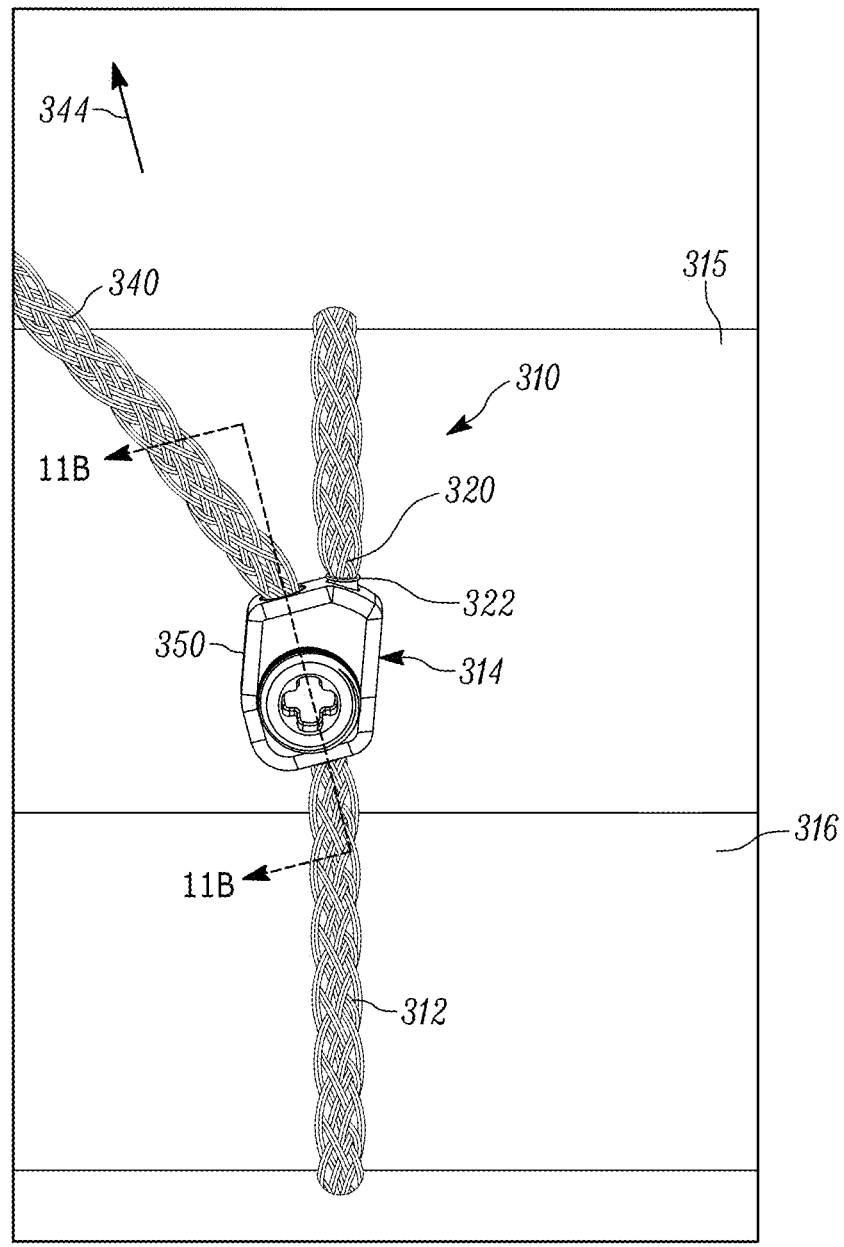
FIG. 11A is a perspective view of a surgical loop showing a connector of the surgical loop and a cable of the surgical loop encircling a pair of bones.

With respect to FIG. 11A, a surgical loop 310 is provided that includes the cable 312 and a connector 314. The cable 312 and the connector 314 are similar in many respects to the surgical cable 24 and the connector 22 discussed above. For example, both the cables 24, 312 may be a loosely-woven cable made of a plurality of elements that each include a plurality of wires or strands of metallic material, such as nitinol, cobalt chrome, titanium or stainless steel. The elements of the cable 312 thereby flatten out against bones 315, 316 and conforms to the outer surfaces of the bones 315, 316 when the cable 312 is tensioned there against. Because the cable 312 flattens out against the bones 315, 316, rather than maintaining a circular-cross section, the tension applied to the cable 312 may be more evenly distributed against the bones 315, 316. In another form, the cable 312 may be a polymer cable having a plurality of strands made of polymer material.

The term loosely-woven cable is intended to refer to a cable that flattens out or otherwise changes its cross-sectional shape to match the contour of bone when the cable is tensioned against the bone under ordinary implant conditions. By contrast, conventional surgical cable generally does not flatten out or conform to bone and instead may, at most, deform slightly to have an elliptical cross section. The elliptical cross section of these conventional surgical cables still results in small contact areas against the bones which may be undesirable in some applications. The loosely-woven cable may also thin and elongate under tension. For example, the loosely-woven cable may have a relaxed, untensioned cross-sectional diameter of roughly 0.100 inch and a cross-sectional diameter of roughly 0.05 inch under tension. The decrease in cross-sectional diameter of the cable may be attributable to the tension drawing the slack out of the loosely woven fibers and reduces the spacing therebetween.

Figure 11B:
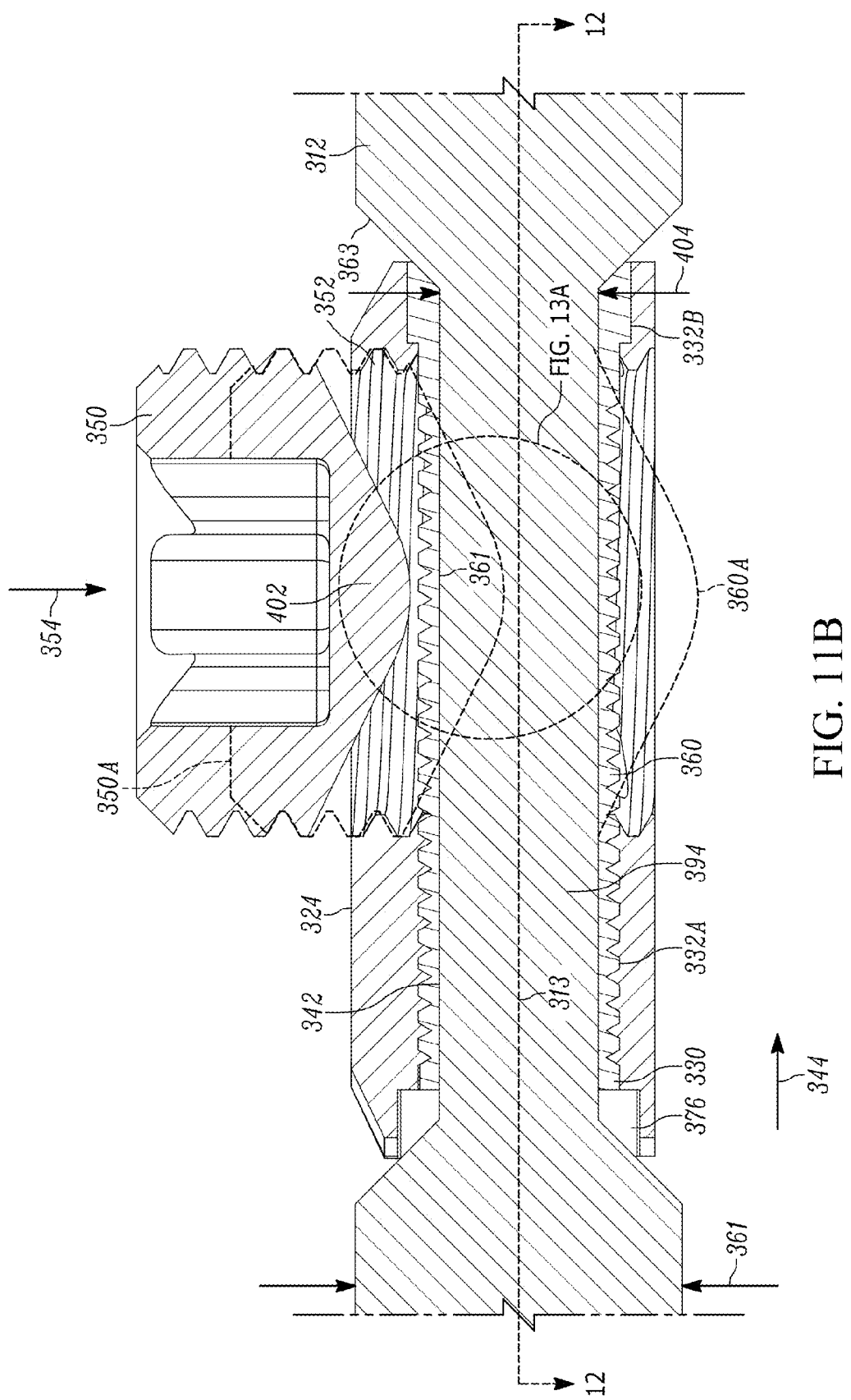
FIG. 11B is a cross-sectional view taken across line 11B-11B in FIG. 11A showing a set screw in a threaded bore of a body of the connector, a deformable sleeve of the connector extending in the body below the set screw, and the cable extending through the sleeve.
Figure 12:
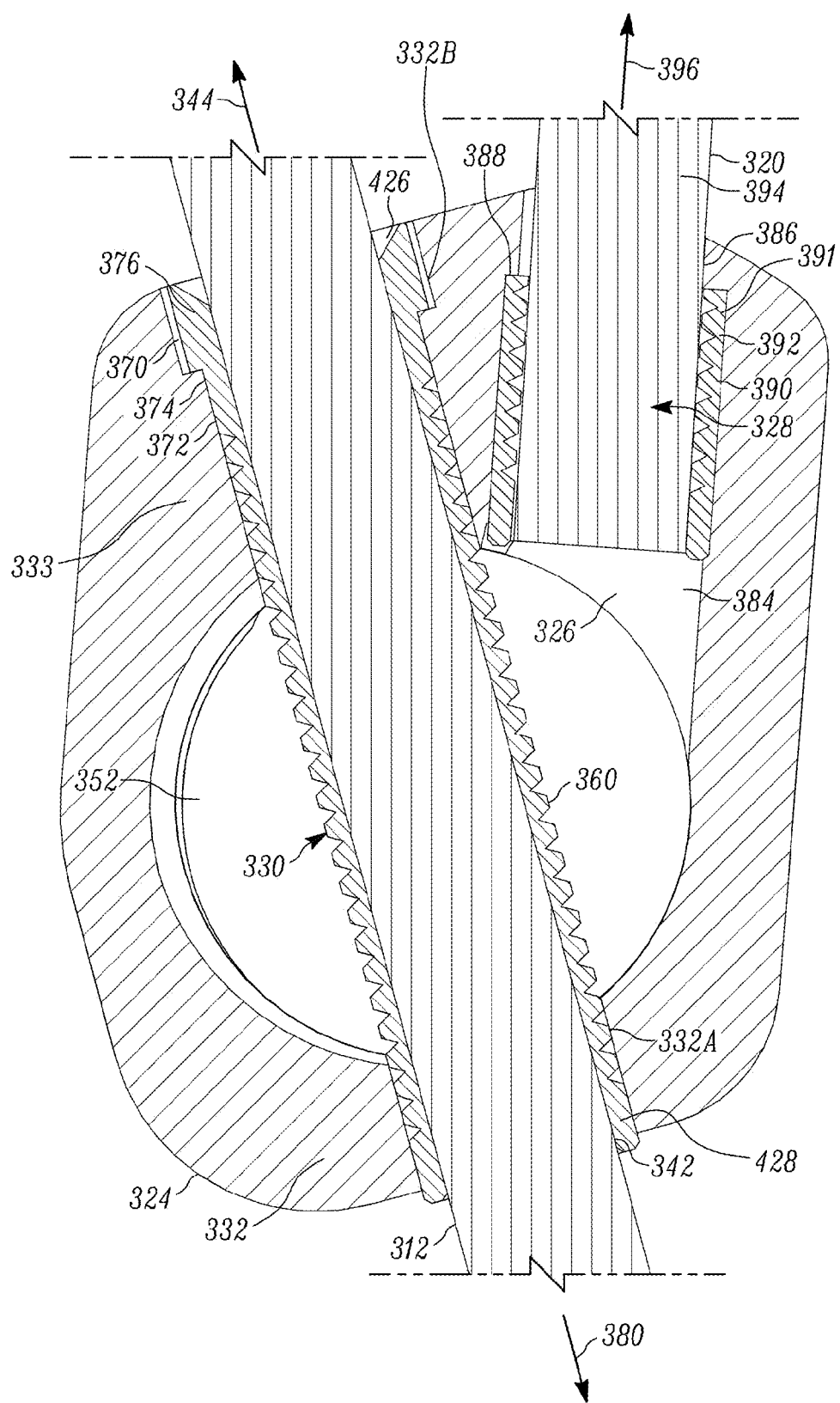
FIG. 12 is a cross-sectional view taken across line 12-12 in FIG. 11B showing one end of the cable extending through the sleeve and a plug of the other end of the cable secured in an adjacent opening of the connector body.

With reference to FIGS. 11A and 12, the cable 312 has a trailing end portion 320 that includes a plug 322 and the connector 314 includes a body 324 with a stop opening 326 for receiving the cable trailing end portion 320. With reference to FIGS. 11B and 12, the connector 314 further includes a deformable locking member, such as a sleeve 330, and the body 324 has sleeve supporting portions 332, 33 for supporting the sleeve 330. The cable 312 has an opposite leading end portion 340 that is advanced through an opening 342 of the sleeve 330 in direction 344 and pulled clear of the connector 314 as shown in FIG. 11A. The cable 312 has a longitudinal axis 313 extending between the end portions 320, 340.

With reference to FIGS. 11B and 12, the connector 314 includes an actuator, such as a set screw 350, connected to the body 324. The set screw 350 has a lower portion that engages the sleeve 330, such as a leading end 402 of the set screw 350. The set screw 350 is positioned above a portion 360 of the sleeve 330 that extends across a set screw bore 352 of the body 324. To fix the connector 314 to the cable 312, the set screw 350 is shifted to a locked position 350A which deforms the sleeve portion 360 downward to a deformed position 360A wherein the sleeve portion 360 has a generally V-shape. The set screw 350 may be threadingly engaged with the body 324 such that tightening the set screw 350 drives the set screw 350 downward in direction 354 and presses the leading end 402 of the set screw 350 against the sleeve portion 360. In another form, the actuator may be a locking cap connected to the body 324 via a cam engagement. For example, the locking cap may have one or more projections that ride in one or more cam slots of the body 324 and permit locking of the cable 312 with less than 360 degrees of rotation of the locking cap, such as less than 270 degrees, or less than 180 degrees. In one form, the locking cap may have a two-piece construction that includes a lower portion that engages the sleeve 330 and an upper portion that is rotatable relative to the lower portion. The upper portion of the locking cap includes one or more flanges that engage the body 324 with turning of the upper portion and cause the lower portion of the locking cap to advance against and deform the sleeve.

Continued tightening of the set screw 350 causes the leading end 402 to deflect the sleeve portion 360 and cable 312 extending therethrough into the generally V-shape. By changing the shape of the sleeve portion 360 and the cable 312 from a straight configuration to a generally V-shaped configuration, the sleeve portion 360 grips the cable 312 more securely because the cable 312 generally has to straighten out before the cable 312 can move longitudinally within the sleeve opening 342. The engagement of the set screw 350 with the body 324 resists the sleeve portion 360, and cable 312 extending therethrough, from straightening out and thereby keeps the cable 312 and the sleeve portion 360 locked in the V-shaped configuration. This rigidly fixes the connector 314 to the cable 312.

In greater detail, any straightening out of the cable 312 while the cable 312 is held to the V-shaped profile (or a different shape) by the set screw 350 and deformed sleeve portion 360 increases the force between the outer surfaces of the cable 312 and an inner surface 407A (see FIG. 13) of the sleeve portion 360 in multiple locations, which increases friction. This friction increases the resistance of the cable 312 to being pulled through the sleeve portion 360. Further, when the cable 312 is held in the V-shape by the set screw 350 and the deformed sleeve portion 360, the elements 394 and strands thereof would need to move and translate amongst themselves in order to permit movement of the cable 312 within the sleeve portion 360. The compressive force applied by the set screw 350 and the deformed sleeve portion 360 causes additional friction between the elements 394 which further increases the resistance of the cable 312 to being pulled through the sleeve 330.

The cable 312 has a relaxed, untensioned outer diameter 361 in the range of approximately 0.105 inches to approximately 0.090 inches, such as approximately 0.1 inches in a free state and the sleeve 330 has an inner diameter 404 in the range of approximately 0.064 inches to approximately 0.061 in inches, such as 0.0625 inches, as shown in FIG. 11B. Due to the inner diameter 404 being smaller than the free state cable diameter 361, the cable 312 includes tapered portions 363 once the cable 312 has been advanced through the sleeve 330. The smaller diameter 404 of the sleeve 330 constricts the elements 394 of the cable 312 within the sleeve portion 360 and removes spacing between the elements 394. This makes the elements 394 easier to grip with deformation of the sleeve portion 360 because the elements 394 are less able to shift out of the path of an upper portion 361 of the sleeve portion 360 as the sleeve portion 360 is crimped onto the cable 312. Driving the set screw 350 to the locked position and deforming the sleeve portion 360 to the deformed position 360A reduces the cross-sectional area of the sleeve opening 342 to be in the range of approximately 30 percent to approximately 60 percent of the original cross-sectional area of the sleeve opening 342. The reduction in the cross-sectional area of the sleeve opening 342 crimps the sleeve portion 360 to the cable 312.

With reference to FIGS. 11B and 12, the sleeve supporting portions 332, 333 of the body 324 includes a pair of aligned openings 332A, 332B. The opening 332B includes an enlarged portion 370, a narrower portion 372, and a collar portion 374. The sleeve 330 includes a flange 376 sized to fit within the enlarged portion 370 and seat against the collar portion 374. The engagement of the flange 376 and the collar portion 374 resists pull-through of the sleeve 330 in direction 380 upon tensioning of the cable 312. Further, the engagement of the flange 376 and the collar portion 374 resists longitudinal movement of the sleeve 330 relative to the body 324 in direction 380 as the set screw 350 is driven and deforms the sleeve portion 360 to the deformed position 360A.

With reference to FIG. 12, the stop opening 326 of the body 324 includes an enlarged portion 384, a narrow portion 386, and a collar 388 configured to engage the plug 328. As discussed below in FIGS. 21-24 with respect to plug 532, the plug 328 may include a wall 390 having inner wall portions 391 and recesses or grooves 392 separating the inner wall portions 391. The plug 328 may be swaged crimped, roller reduction, or otherwise mechanically reduced onto the elements 394 of the cable end portion 320 to secure the plug 328 thereto. The reduction operation reduces an inner diameter of the plug 328 and causes portions of the elements 394 to extend radially outward into the grooves 392 and creates interference between the elements 394 and the plug 328. This provides improved pull-through resistance of the elements 394 from the plug 328 and further strengthens the connection between the cable end portion 320 and the body 324.

Figure 13A:
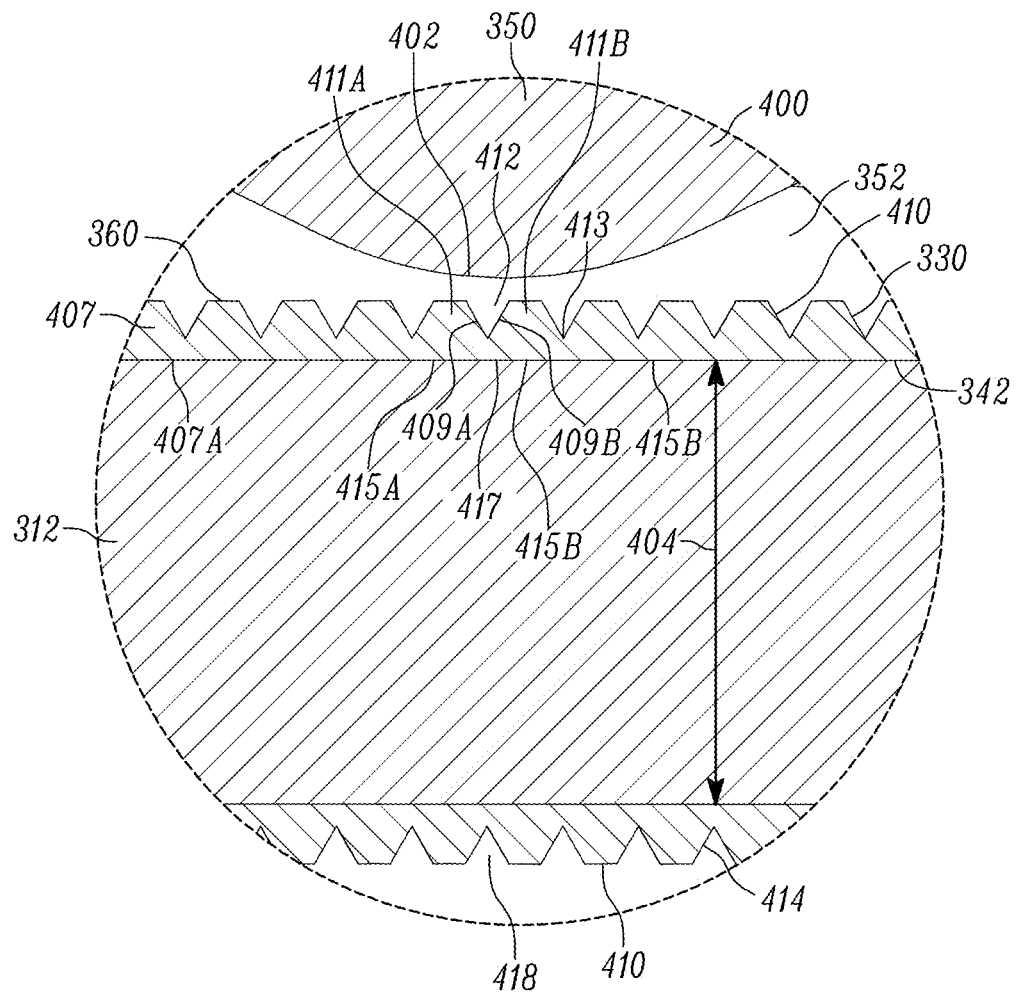
FIG. 13A is an enlarged view of the circled area in FIG. 11B showing a wall of the sleeve having thicker portions and thinner portions in an alternating configuration along the sleeve.
Figure 14:
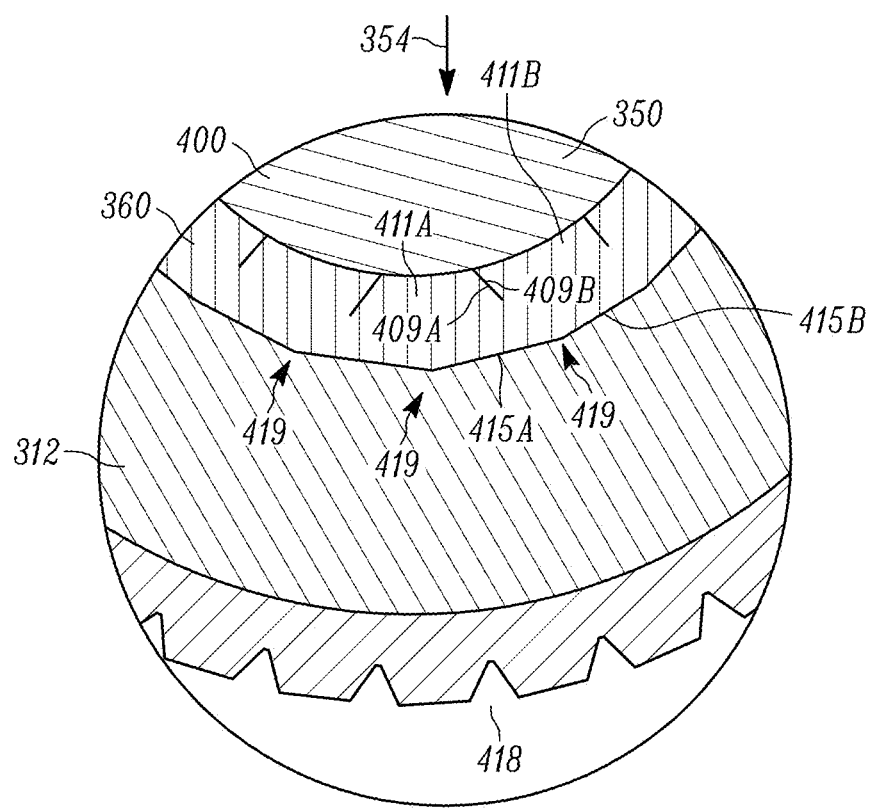
FIG. 14 is a view similar to FIG. 13A showing the set screw driven to a locked position which deforms the sleeve and forms ridges on an inner surface of the sleeve that engage the cable.

Turning to FIGS. 13A and 14, the sleeve portion 360 includes an annular wall 407 having the inner surface 407A extending about the opening 342 of the sleeve 330. The wall 407 includes thicker portions 411A, 411B and thinner portions 413 in an alternating arrangement along the wall 407 that operate to form one or more ridges 419 upon shifting of the set screw 350 to the locked position that generally form line contacts extending around the cable 312. Further, the ridges 419 create areas of higher compressive stress in the cable 312 which may deform the cable 312 where the ridges 419 engage the cable 312. In this manner, the ridges 419 engage the cable 312 and provide a strong grip therewith once the set screw 350 has deformed the sleeve portion 360.

The ridges 419 separate discrete segments of the inner surface 407A of the sleeve portion 360 and are formed by the different amounts of deformation in the thicker portions 411A, 411B and the thinner portions 413. More specifically, the inner surface 407A of the sleeve 330 may be formed by inner surface portions 415A, 415B, 417 of the thicker portions 411A, 411B and thinner portions 413. In FIG. 13A, the sleeve portion 360 is shown undeformed such that inner surface portions 415A, 415B of the thicker portions 411A, 411B and inner surface portions 417 of the thinner portions 413 are coaxially aligned to form a smooth, cylindrical shape of the inner surface 407A. Further, the thicker portions 411A, 411B have sides 409A, 409B spaced apart by take up gaps 412.

Driving the set screw 350 to the locked position deforms the sleeve portion 360 into the generally V-shape as shown in FIG. 14. The thinner portions 413 deform more than the thicker portions 411A, 411B which permits the thicker portions 411A, 411B to articulate relative to each other and which decreases the size of the take up gaps 412 until the sides 409A, 409B abut each other. Further, because the thinner portions 413 deform more than the thicker portions 411A, 411B, the inner surface portions 417 of the thinner portions 413 deform more than the inner surface portions 415A, 415B of the thicker portions 411A, 411B. In this manner, the inner surface portions 415A, 415B each maintain a generally annular shape whereas the inner surface portions 417 deform to a more elbow-joint shape. This forms ridges 419 on the upper side of the sleeve portion 360 that engage the cable 312 and resist longitudinal movement of the cable 312 within the sleeve 330.

The connector 314 utilizes multiple locking features to secure the connector 314 to the cable 312. Specifically, driving the set screw 350 to the locked position fixes the connector 314 to the cable 312 by decreasing the inner diameter 404 of the sleeve 330, deforming the sleeve portion 360 and cable 312 extending therethrough into a generally V-shape, and engaging inner ridges 419 of the sleeve portion 360 with the cable 312. In this manner, the connector 314 can be rigidly fixed to the cable 312 despite the cable 312 being loosely woven. In one form, the thicker portions 411A, 411B include a plurality of ribs extending around the sleeve 330 and spaced apart by the gaps 412. In another form, the thicker portions 411A, 411B may be portions of a single or multiple helical thread, for example.

Figure 13B:
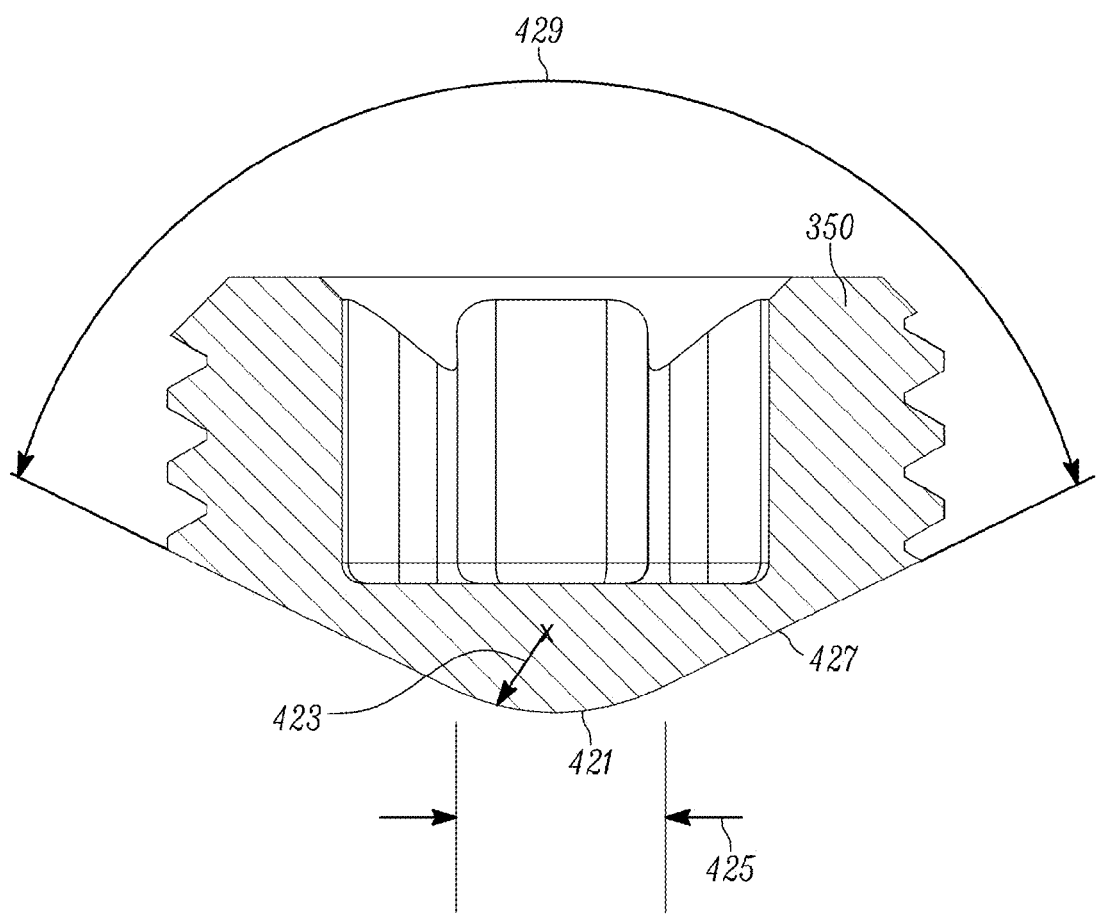
FIG. 13B is a cross-sectional view of the set screw of FIG. 11B showing a radiused leading end of the set screw that contacts the sleeve with driving of the set screw.

Turning to FIG. 13B, the leading end 402 of the set screw 350 includes a partially spherical nose 421 with a radius 423 in the range of approximately 0.05 inches to approximately 0.06 inches, such as approximately 0.057 inches. The nose 421 may have a diameter 425 in the range of approximately 0.4 inches to approximately 0.6 inches, such as approximately 0.5 inches. Further, the leading end 402 includes a conical surface 427 having a taper with an angle 429 in the range of 120 degrees to approximately 140 degrees, such as approximately 128 degrees. The nose 421 provides an initial stage of deformation of the sleeve portion 360 that requires less torque to be applied to the set screw 350 and the conical surface 427 provides further deformation of the sleeve portion 360 and requires more torque to be applied to the set screw 350. The set screw 350 thereby provides increasing tactile resistance to continued driving toward the locked position thereof which allows a user to tighten the set screw 350 by feel, with the use of a torque limiting tool to a desired locking of the cable 312. In another approach, a rotation limiting tool may be used to ensure that the set screw 350 has been fully driven to a locked position.

Figure 15:
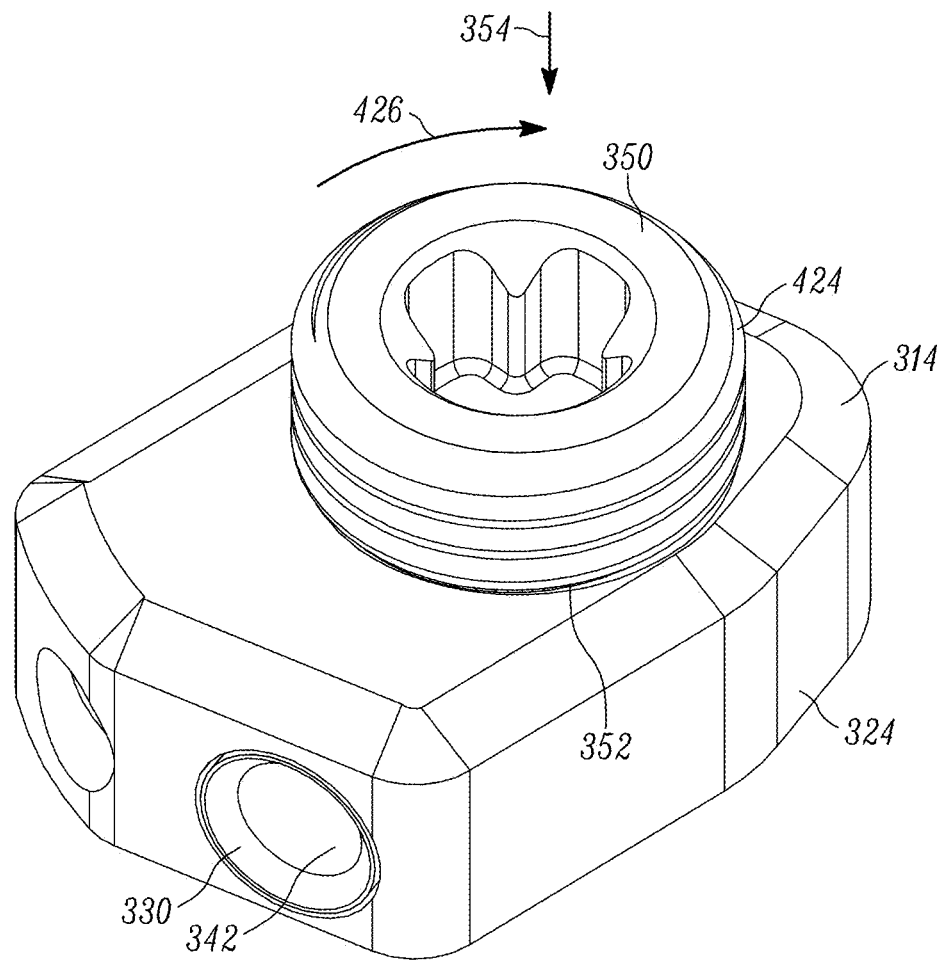
FIG. 15 is a perspective view of the connector of FIG. 12 showing the set screw in a proud, unlocked position extending upward from the body of the connector.
Figure 16:
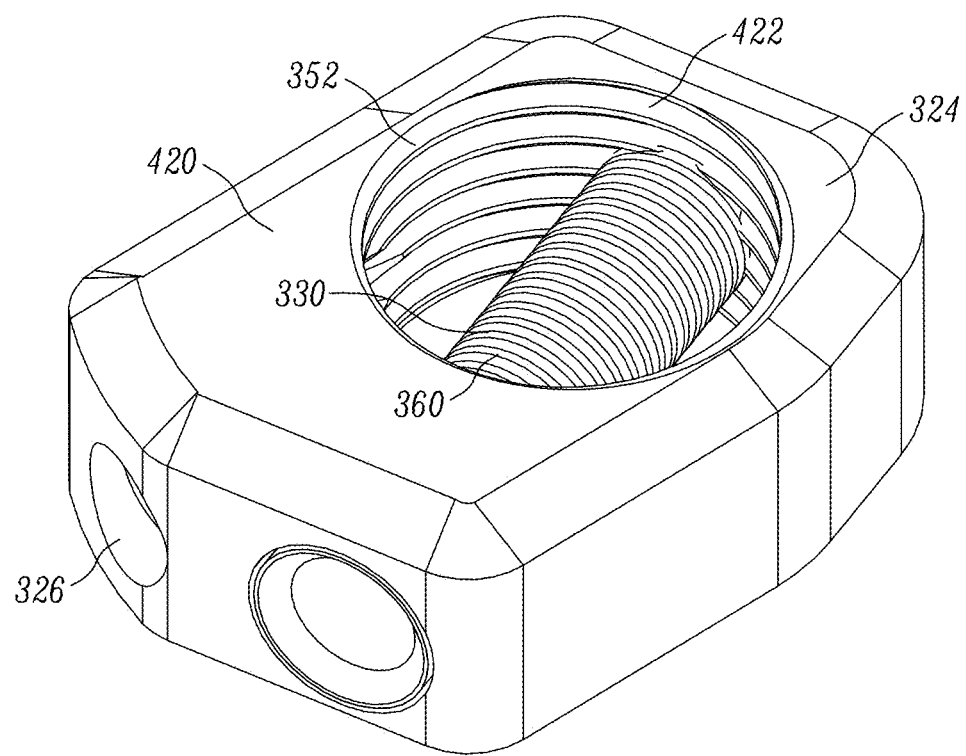
FIG. 16 is a perspective view similar to FIG. 15 with the set screw removed to show the deformable sleeve extending across the set screw bore of the connector body.
Figure 17:
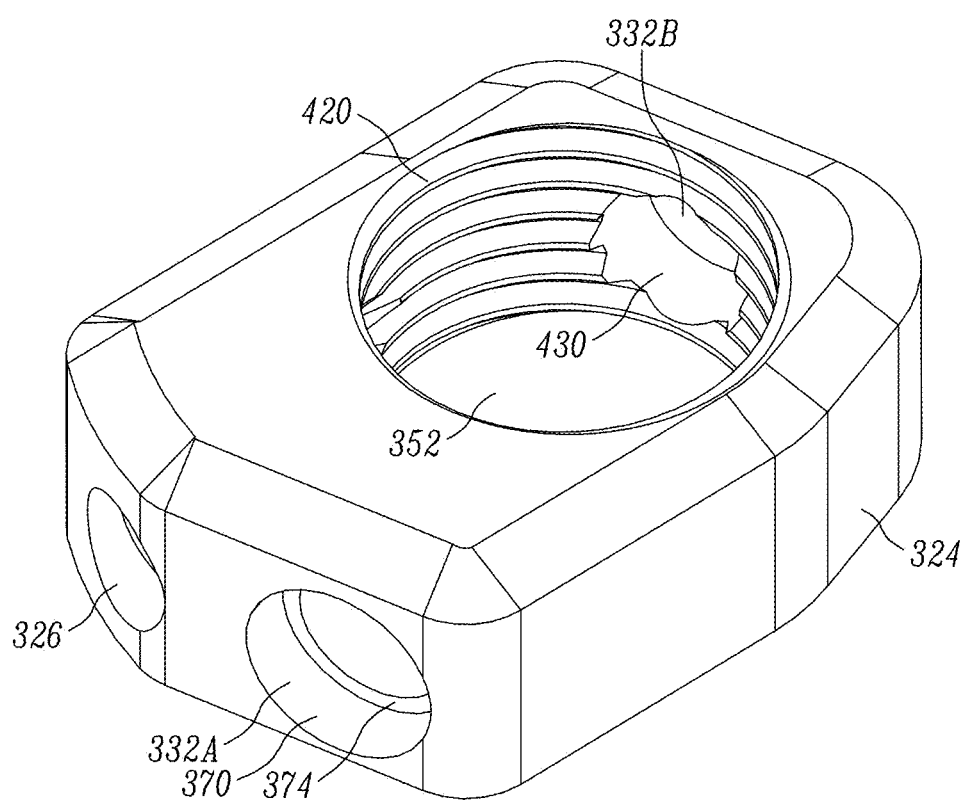
FIG. 17 is a perspective view similar to FIG. 15 with the deformable sleeve removed to show aligned openings of the connector body on either side of the set screw bore for receiving opposite ends of the deformable sleeve.

With reference to FIGS. 15-17, the body 324 includes a wall 420 extending about the set screw bore 352. In one form, the wall 420 includes a rotary locking structure, such as threads 422, which may engage with corresponding threads 424 of the set screw 350. In this manner, turning of the set screw 350 in direction 426 causes the set screw 354 to travel in direction 354 against the sleeve portion 360 generally in direction 354. As the sleeve portion 360 is deformed into the V-shape by the set screw 350, the opposite ends 426, 428 of the sleeve 330 remain supported by the body 324 (see FIG. 12). Specifically, the flange 376 of the end 426 engages the neck-down portion 374 and the end 428 is supported by a portion 430 (see FIG. 17) of the wall 420. In this manner, the ends 426, 428 of the sleeve 330 are supported by the body 324 while the sleeve portion 360 extending across the set screw bore 352 and the cable 312 extending therein are deflected into the generally V-shape by the set screw 350.

The connector 314 is made of biocompatible materials that are sufficiently strong to provide fixation of the cable 312. For example, the body 324, sleeve 330, and set screw 350 may be made of 316L stainless steel. As another example, a portion or all of the connector 314 may be made of Titanium or another metallic material.

Figure 18:
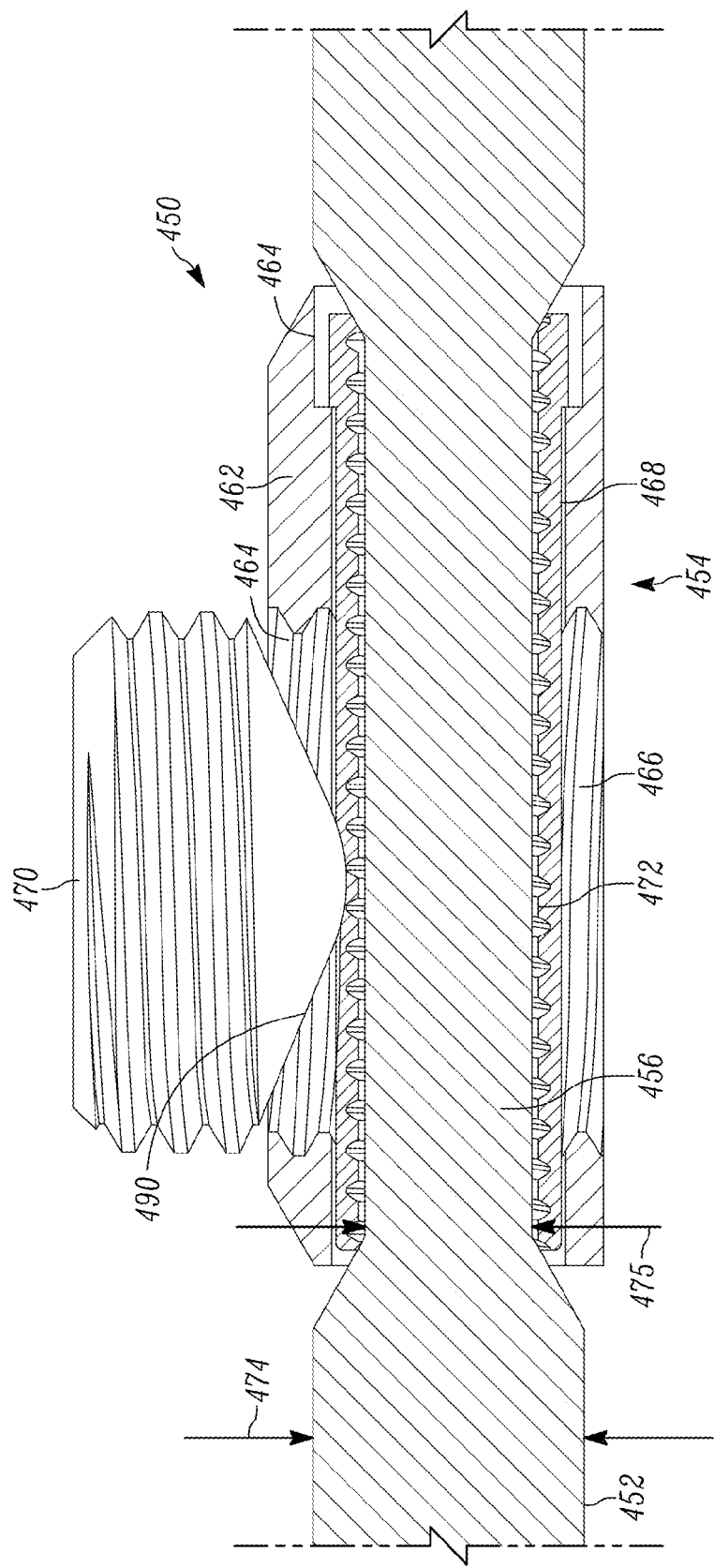
FIG. 18 is a cross-sectional view of a portion of another surgical loop showing a cable and a connector of the surgical loop, the connector having a deformable sleeve with a wall that includes inner wall portions and inner grooves separating the inner wall portions.

With reference to FIGS. 18 and 19, a surgical loop 450 as provided that is similar in many respects to the surgical loop 310 discussed above. The surgical loop 450 includes a loosely-woven cable 452 and a connector 454 through which a length or portion 456 of the cable 452 extends. As discussed above with respect to the surgical loop 310, one end of the cable 452 is secured to the connector 454 by way of a plug/stop opening arrangement and the other end of the cable 452 is secured to the connector 454 using a deformable sleeve 468 and set screw 470 of the connector 454. The connector 454 includes a body 462 having a throughbore 464. The deformable sleeve 468 extends across the throughbore 466. The set screw 470 may be threadingly engaged with the body 462 such that driving the set screw 470 to a locked position causes a leading end 490 of the set screw 470 to deform the sleeve 468 and cable 452 extending therethrough.

The sleeve 468 includes an opening 472 with a diameter 475 that is smaller than a relaxed, untensioned diameter 474 of the cable 452. In this manner, advancing the portion 456 of the cable 452 into the sleeve opening 472 constricts the cable portion 456 within the sleeve 468. By constricting the cable portion 456, the elements of the cable 452 are more tightly bound together and thus are more constricted against movement away from the crimping action applied by the set screw 470. Thus, by reducing the cable portion 456 down to the diameter 475 within the sleeve 468, the portions of the cable 452 outside of the connector 454 may flatten out against bones whereas the cable portion 456 within the connector 454 is more tightly bundled and thus are more easily engaged by the sleeve 468 as the set screw 470 crimps the sleeve 468 onto the cable portion 456.

With respect to FIGS. 19 and 20, another aspect of the connector 454 that improves the grip of the sleeve 468 on the cable 452 is that the sleeve 468 includes a wall 480 with one or more recesses or grooves 482. The grooves 482 separate one or more inner wall portions 483 that extend around the cable 452 and grip the cable 452 once the set screw 470 has deformed the sleeve 468. The inner wall portions 483 may have a polygonal shape and edges 485 extending transversely to and around the cable 452 extending through the sleeve 468. The grooves 482 and inner wall portions 483 provide a secure grip of the sleeve 468 on the cable 452.

More specifically, deforming the sleeve 468 with the set screw 470 causes an outer portion 520 of the cable 452 to bulge outwardly into the grooves 482 of the wall 480 as shown in FIGS. 19 and 20. Because the edges 485 extend transversely to the length of the cable 452 and around the cable 452, the edges 485 of the inner wall portions 483 engage the bulging cable outer portions 520 of the cable 452 with greater force as the tension in the cable 452 is increased. Like the ridges 419 discussed above, the inner wall portions 483 and the edges 485 thereof generally form line contacts with the cable 452 that extend around the circumference of the cable 452. The engagement of the edges 485 with the cable outer portions 520 resist pull-through of the cable 452 in direction 487 as shown in FIG. 20. Thus, the interference between the cable outer portions 520, grooves 482, and inner wall portions 483 interlocks the cable 452 with the sleeve 468. In this manner, the connector 454 may be securely fixed to the cable 452 despite the cable 452 being loosely-woven. Further, the interference between the cable outer portions 520, grooves 482, and inner wall portions 483 is provided whether the cable 452 is under tension as the set screw 470 is driven to the locked position or the cable 452 is tensioned after the set screw 470 has been driven to the locked position.

In one form, the inner walls 483 are a plurality of spaced walls each extending continuously around the circumference of the cable 452. In another form, the inner walls 483 are a plurality of spaced walls that each include breaks in the inner wall portions 483 such that the wall 483 is discontinuous around the circumference of the cable 452. In yet another form, there is a single helical groove 482 and associated single or multiple helical thread extending along the length of the sleeve 468. The inner wall portions 483 may be portions of the single or multiple helical thread.

With reference to FIG. 19, the set screw 470 has been driven downward in direction 486 which engages the leading end 490 of the set screw 470 against an outer surface 492 of the sleeve wall 480. The leading end 490 of the set screw 470 has a generally V-shaped profile similar to the leading end 402 of the set screw 350. Driving the set screw 470 to the locked position deforms the sleeve 468 and cable portion 456 extending therein into a generally V-shape that corresponds to the profile of the leading end 490 of the set screw 470. This deformation of the sleeve 468 causes the cable portion 456 extending through the sleeve 468 to be pinched between points 502, 504, 506. This three-point pinching of the cable 452 provides multiple locations of rigid connection between the sleeve 468 and the cable 452. Further, because the cable 452 is deformed into the generally V-shaped configuration shown in FIG. 19, the sleeve 468 and the cable 452 generally must flatten out and become straight before the cable 452 can slide relative to the deformed sleeve 468. The engagement of the set screw 470 and the body 462 resist return of the sleeve 468 and cable 452 away from the V-shape and thereby resist sliding of the cable 452 within the sleeve 468.

Figure 21:
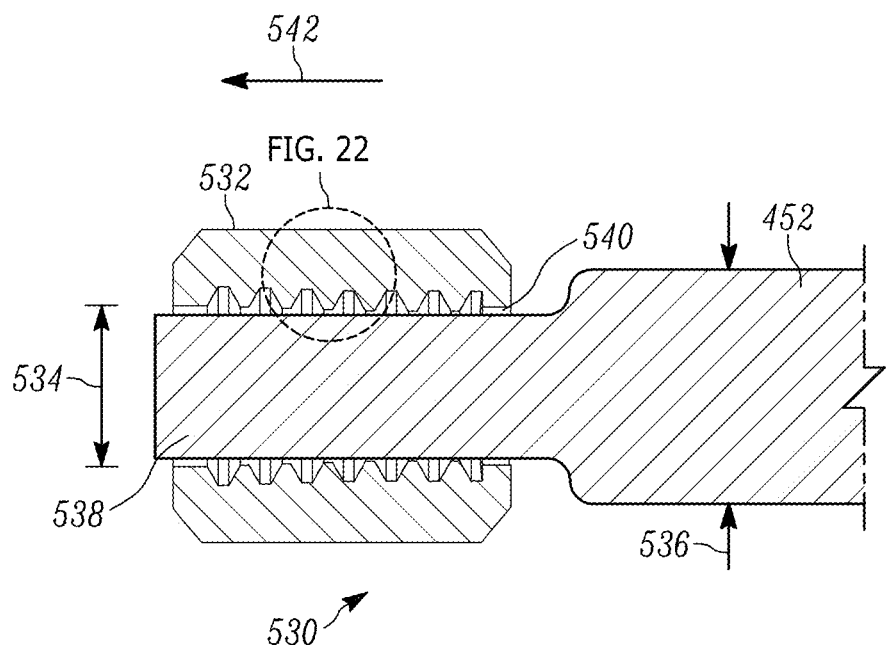
FIG. 21 is a cross-sectional view of an end portion of the cable of FIG. 18 showing a plug positioned on wires of the cable prior to a swaging operation being performed to secure the plug to the cable wires.
Figure 22:
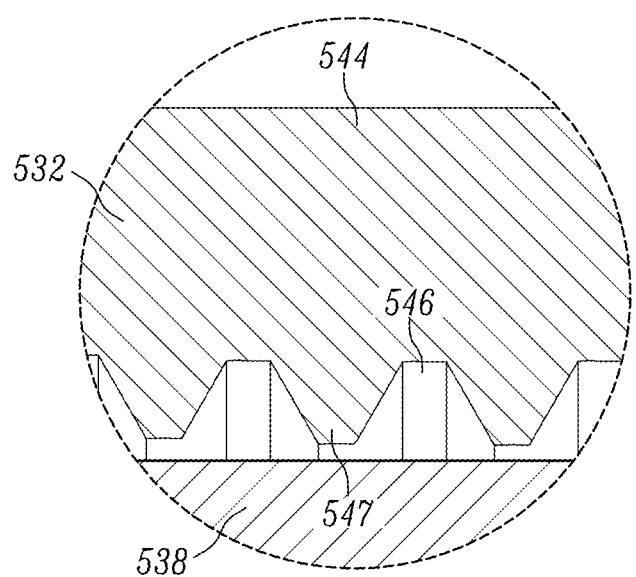
FIG. 22 is an enlarged view of the circled area in FIG. 21 showing strands of the cable end portion and inner grooves of the plug.

With reference to FIGS. 21 and 22, the cable 452 may include an end portion 530 with a plug 532. The plug 532 has a wall 544 with grooves 546 separating inner wall portions 547. The plug 532 is swaged, crimped, rolled, or otherwise mechanically reduced onto elements 538 of the cable 452 to secure the plug 532 thereto. Like the sleeve 468, the plug 532 has an inner diameter 534 that is smaller than a relaxed, outer diameter 536 of the cable 452. To connect the plug 532 to the elements 538 of the cable 452, the elements 538 are advanced into an opening 540 of the plug 532 in direction 542 which constricts the elements 538 to the diameter 534, which is less than the loose outer diameter 536.

Figure 23:
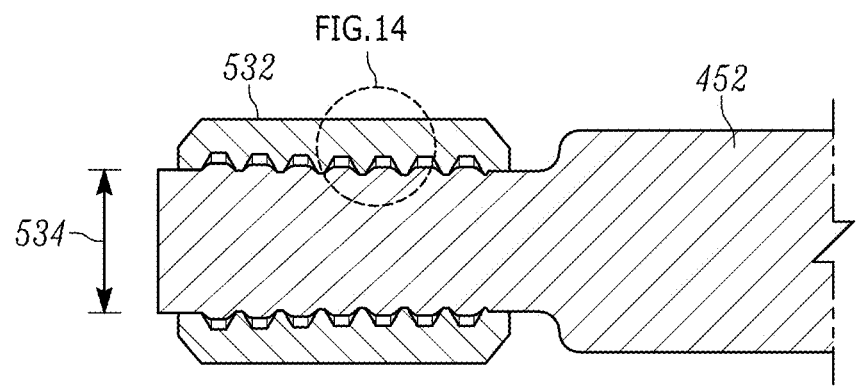
FIG. 23 is a cross-sectional view similar to FIG. 21 showing the plug having been swaged onto the strands of the cable end portion.
Figure 24:
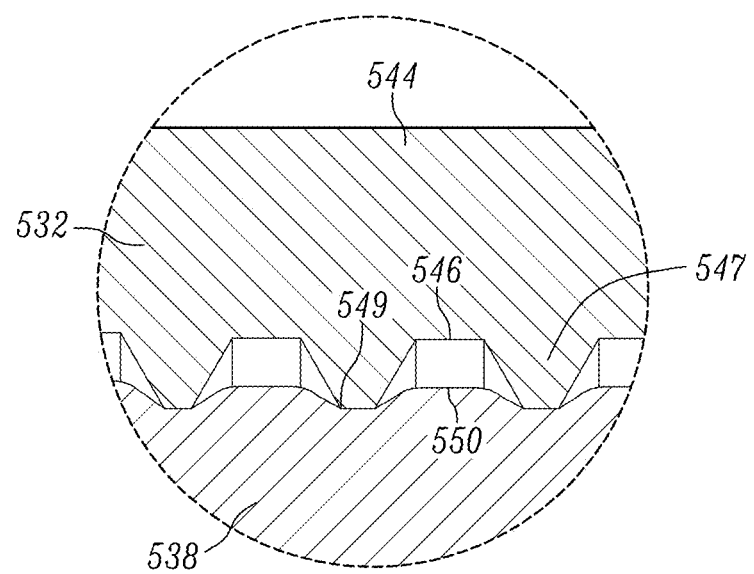
FIG. 24 is an enlarged view of the circled area in FIG. 23 showing the strands of the cable end portion interlocking with the inner grooves of the plug.

With reference to FIGS. 23 and 24, swaging or reducing the plug 532 onto the elements 538 of the cable 452 reduces the inner diameter 534 of the plug 532 and tightly engages the wall 544 with the elements 538. The cable 452 includes outer portions 550 that are forced into the grooves 546 by way of the swaging or other mechanical reduction operation and creates interference between the surgical cable 452 and the plug 532. The inner wall portions 547 include edges 549 that engage the cable outer portions 550 and resist movement of the cable 452 relative to the plug 532. In this manner, the loosely-woven cable 452 is interlocked with the grooves 546 of the plug 532.

Various alterations to the embodiments discussed above are within the teachings of the present disclosure. For example, a connector in accordance with the connector 314 discussed above may be provided with a deformable sleeve that includes both the thicker and thinner portions 411A, 411B and 413 as well as the inner wall portions 483 discussed above with respect to the connector 462.

Figure 25:
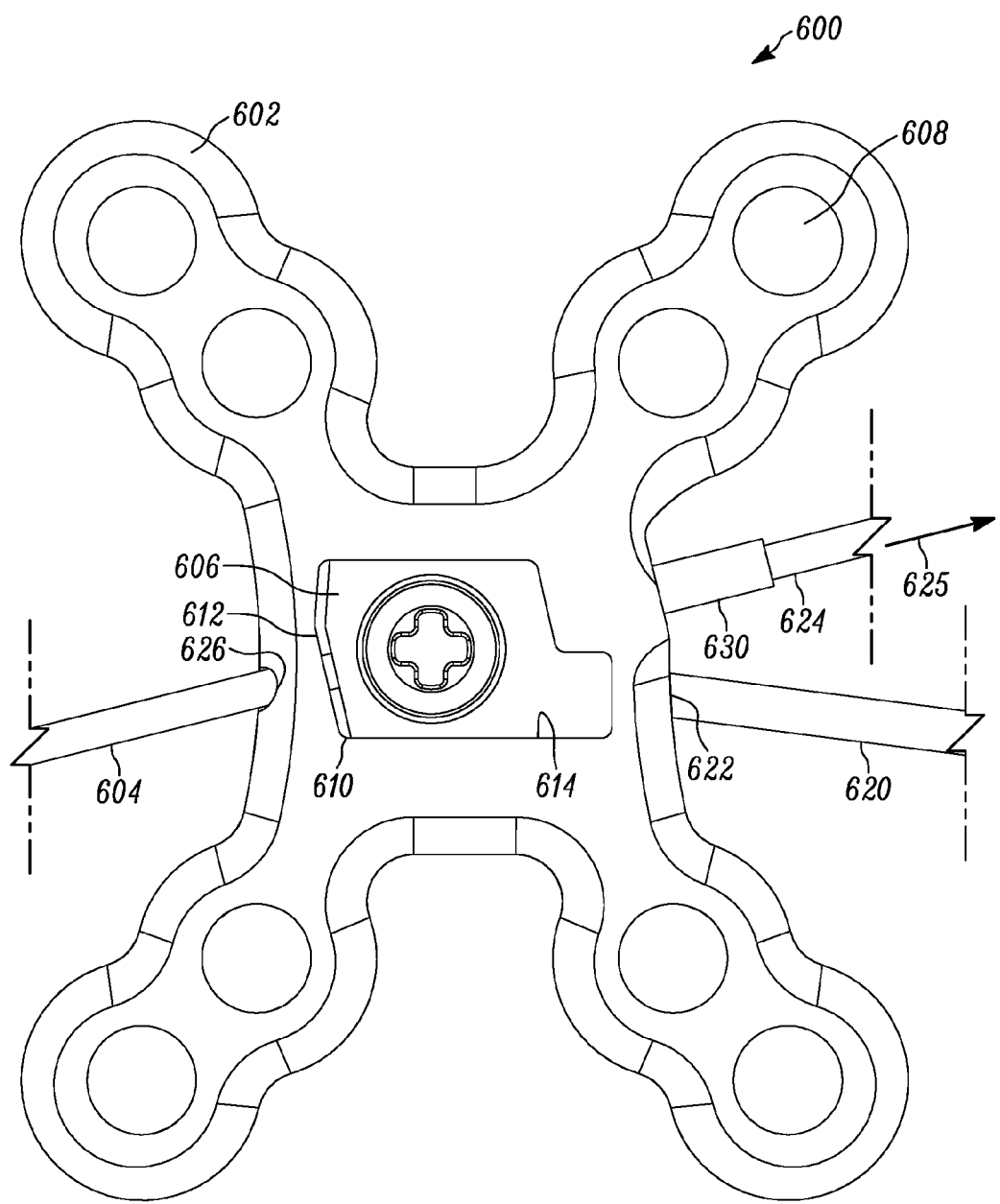
FIG. 25 is a perspective view of a bone plate system having a bone plate with a recess that receives a connector of the bone plate system.

Turning to FIG. 25, a bone plate system 600 is provided including a bone plate 602, a surgical cable 604, and a connector 606. The bone plate 602 is similar in many respects to the bone plate 16 discussed above and includes throughbores 608 for receiving bone screws. The connector 606 is similar in many respects to the connector 22 discussed above. The bone plate 602 and connector 606 are assembled rather than being integrally formed. The bone plate 602 includes a recess 610 and walls 612 extending about the recess 610. The connector 606 has peripheral walls 614 for abutting the walls 612 and transferring loading from the surgical cable 604 to the bone plate 602 and vice versa.

The surgical cable 604 includes a trailing end portion 620 extending through an opening 622 of the bone plate 602 and into the connector 606. The surgical cable 604 has a leading end portion 624 that is looped around bone portions and advanced in direction 625 through an opening 626 of the bone plate 602, through the connector 606, and outward through a sleeve 630 of the bone plate 602. The sleeve 630 is, in one form, a cannulated metallic cylinder.

The sleeve 630 improves the ease of cutting the surgical cable 604 during an emergent re-entry procedure because the sleeve 630 allows a user to cut through the multi-strand metallic surgical cable 604 using standard shear or pinch-style instruments rather than requiring a specialized cable cutter. The sleeve 630 has an inner diameter that reduces the outer diameter of the surgical cable 604 to a near solid-state configuration. When a shear or pinch-style instrument contacts the sleeve, the sleeve 630 puts additional compression on the surgical cable 604. The sleeve 630 thereby applies holds the fine strands of the surgical cable 604 together and restricts relative motion of the strands which would allow the strands to escape the shear. For a pinch style cutting instrument, the jaws of the instrument compress the individual strands pre-compressed by the sleeve 630. This makes the cutting operation more effective because all of the strands tend to fail and shear at once rather than a few of the strands remaining intact.

Those skilled in the art will recognize that a wide variety of modifications, alterations, and combinations can be made with respect to the above-described embodiments without departing from the spirit and scope of the invention, and that such modifications, alterations, and combinations are to be viewed as being within the scope of the claims.

What is claimed is:

1. An apparatus for securing bone portions, the apparatus comprising:
    a surgical cable having an effective outer diameter and including a plurality of elongate elements; and
    a connector comprising:
        a body;
        a deformable sleeve associated with the body and having a through opening for receiving the surgical cable, the through opening having a non-deformed configuration wherein the through opening has an initial inner diameter smaller than the effective outer diameter of the surgical cable to compress the elements of the surgical cable together with the surgical cable extending in the sleeve through opening; and
        an actuator connected to the body and operable to deform the sleeve and further compress the compressed elements of the surgical cable therein to secure the surgical cable relative to the body.

2. The apparatus of claim 1 wherein the initial inner diameter of the deformable sleeve through opening is sized to compress the surgical cable as the surgical cable is advanced into the through opening from a free state configuration to a near solid state configuration.

3. The apparatus of claim 1 wherein the inner diameter of the deformable sleeve through opening is seventy percent or less than the effective outer diameter of the surgical cable.

4. A bone plate system comprising a plurality of bone screws and a bone plate that includes the apparatus of claim 1, the bone plate including a bone plate body having a plurality of throughbores for receiving the bone screws.

5. The bone plate of claim 4 wherein the bone plate body and the connector body are monolithically formed from a single piece of material.

6. The apparatus of claim 1 wherein the elongate elements of the surgical cable each include a plurality of elongate monolithic strands.

7. The apparatus of claim 1 wherein the elongate elements of the surgical cable comprise elongate monolithic strands of metallic or polymer material.

8. The apparatus of claim 1 wherein the deformable sleeve has opposite ends and a tubular side wall extending from one end of the deformable sleeve to the other end.

9. The apparatus of claim 1 wherein the surgical cable has a free state configuration wherein the elongate elements surround an interior void of the surgical cable and the surgical cable has gaps separating the elongate elements from each other, the surgical cable further having a solid state configuration wherein the elongate elements contact each other and the gaps are closed.

10. An apparatus for securing bone portions, the apparatus comprising:
    a surgical cable; and
    a connector comprising:
        a body having an upper surface and a lower surface;
        a throughbore of the body extending laterally through the body;
        a deformable sleeve in the throughbore of the body and having a through opening for receiving the surgical cable;
        an actuator connected to the body and having a lower portion adapted to be shifted in a longitudinal direction transverse to the surgical cable between unlocked and locked positions to contact the deformable sleeve and deform the surgical cable extending therein;

a lower opening of the body that opens to the lower surface of the body and is in communication with the throughbore of the body; and sleeve support portions of the body on opposite sides of the lower opening from each other, the sleeve support portions supporting the deformable sleeve and being laterally outwardly spaced from the actuator lower portion to permit the actuator lower portion to bend at least a portion of the deformable sleeve and the surgical cable therein into the lower opening and the lateral spaces between the sleeve support portions and the actuator lower portion as the actuator is shifted downward in the longitudinal direction.

11. The apparatus of claim 10 wherein the actuator lower portion includes a recess adapted to permit a portion of the deformable sleeve to deform into the recess as the actuator lower portion shifts between the unlocked and locked positions thereof.

12. The apparatus of claim 10 wherein the actuator lower portion includes an annular wall adapted to contact and deform the deformable sleeve as the actuator lower portion is driven between unlocked and locked positions.

13. The apparatus of claim 10 wherein the actuator lower portion contacts the deformable sleeve intermediate the sleeve support portions of the body and forms neckdown portions of the deformable sleeve that extend through the lateral spaces between the sleeve support portions and the actuator lower portion as the actuator lower portion shifts to the locked position thereof.

14. The apparatus of claim 10 wherein the body includes a second throughbore that receives the actuator and the lower opening separating the sleeve support portions is a lower portion of the second throughbore.

15. The apparatus of claim 10 wherein the surgical cable includes a plurality of elements each comprising a plurality of strands and the through opening of the deformable sleeve is sized to compress the elements of the surgical cable together with the surgical cable extending in the sleeve through opening.

16. The apparatus of claim 10 wherein the surgical cable is tubular.

17. A bone plate system comprising a bone plate including the apparatus of claim 10 and a plurality of bone screws, the bone plate including a bone plate body having a plurality of throughbores for receiving the bone screws.

18. A method of securing bone portions, the method comprising:

positioning a surgical cable about bone portions, the surgical cable having an effective outer diameter and including a plurality of elongate elements;

advancing the surgical cable into a through opening of a deformable sleeve of a connector, the through opening having a non-deformed configuration wherein the through opening has an initial inner diameter smaller than the effective outer diameter of the cable;

compressing elements of the surgical cable together using the smaller initial inner diameter of the through opening of the deformable sleeve of the connector as the surgical cable is advanced into the deformable sleeve of the connector; and securing the surgical cable to the connector.

19. The method of claim 18 wherein compressing the elements of the surgical cable together includes compressing the elements from a free state configuration to a near solid state configuration.

20. The method of claim 18 wherein securing the surgical cable to the connector includes operating an actuator of the connector to deform the deformable sleeve and crimp the surgical cable therein.

21. The method of claim 18 wherein securing the surgical cable to the connector includes shifting a lower portion of an actuator of the connector in a longitudinal direction and deforming the deformable sleeve and surgical cable therein into lateral spaces between the actuator lower portion and sleeve supporting portions of the connector.

22. The method of claim 18 wherein securing the surgical cable to the connector includes shifting an actuator of the connector between unlocked and locked positions and deforming a portion of the deformable sleeve into a recess of the actuator.

23. The method of claim 18 wherein securing the surgical cable to the connector includes shifting an annular wall of an actuator of the connector to deform the deformable sleeve extending about the surgical cable.

24. The method of claim 18 further comprising driving bone screws through bores of a bone plate associated with the connector and into the bone portions.

* * * * *